US007018841B1

(12) United States Patent
Ueda et al.

(10) Patent No.: US 7,018,841 B1
(45) Date of Patent: Mar. 28, 2006

(54) COMPOSITIONS AND METHODS FOR THE INHIBITION OF NEUROTRANSMITTER UPTAKE OF SYNAPTIC VESICLES

(75) Inventors: Tetsufumi Ueda, Ann Arbor, MI (US); Eric D. Özkan, Grosse Pointe Woods, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 1152 days.

(21) Appl. No.: 09/613,170

(22) Filed: Jul. 10, 2000

Related U.S. Application Data

(62) Division of application No. 08/840,006, filed on Apr. 15, 1997, now Pat. No. 6,127,520.

(51) Int. Cl.
*G01N 33/00* (2006.01)
*C07K 14/435* (2006.01)

(52) U.S. Cl. .......................... 436/86; 436/91; 436/106; 436/119; 436/124; 436/139; 436/145; 530/350; 514/2; 435/69.1

(58) Field of Classification Search ................. 436/86, 436/91, 106, 119, 124, 139, 145; 530/350; 514/2; 435/69.1
See application file for complete search history.

(56) References Cited

U.S. PATENT DOCUMENTS

| 4,557,934 | A | 12/1985 | Cooper |
| 4,895,727 | A | 1/1990 | Allen |
| 5,051,448 | A | 9/1991 | Shashoua |
| 5,169,862 | A | 12/1992 | Burke, Jr. et al. |
| 5,182,262 | A | 1/1993 | Leto |
| 5,192,746 | A | 3/1993 | Lobl et al. |
| 5,482,996 | A | 1/1996 | Russell et al. |
| 5,529,914 | A | 6/1996 | Hubbell et al. |
| 5,539,085 | A | 7/1996 | Bischoff et al. |
| 5,559,103 | A | 9/1996 | Gaeta et al. |
| 5,567,435 | A | 10/1996 | Hubbell et al. |
| 5,567,612 | A | 10/1996 | Vacanti et al. |
| 5,573,528 | A | 11/1996 | Aebischer et al. |
| 5,573,934 | A | 11/1996 | Hubbell et al. |
| 5,576,423 | A | 11/1996 | Aversa et al. |
| 5,601,844 | A | 2/1997 | Kagayama et al. |
| 6,127,520 | A * | 10/2000 | Ueda et al. ................. 530/350 |

OTHER PUBLICATIONS

Nakanishi (1992) "Molecular Diversity of Glutamate Receptors and Implications for Brain Function," Science 258:597-603.
Coyle and Puttfarcken (1993) "Oxidative Stress, Glutamate, and Neurodegenerative Disorders," Science 262:689-695.
Bashir et al. (1993) "Induction of LTP in the hippocampus needs synaptic activation of glutamate metabotropic receptors," Nature 363:347-350.
Naito and Ueda (1983) "Adenosine Triphosphate-dependent Uptake of Glutamate into Protein 1-associated Synaptic Vesicles," J. Biol. Chem. 258:696-699.
Tabb and Ueda (1991) "Phylogenetic Studies on the Synaptic Vesicle Glutamate Transport System," J. Neurosci. 11:1822-1828.
Storm-Mathison et al. (1983) "First visualization of glutamate and GABA in neurones by immunocytochemistry," Nature 301:517-520.
Nicholls and Sihra (1986) "Synaptosomes possess an exocytotic pool of glutamate," Nature 321:772-773.
McMahon and Nicholls (1991) "The bioenergetics of neurotransmitter release," Biochim. Biophys. Acta 1059: 243-264.
Kish and Ueda (1991) "Calcium-dependent release of accumulated glutamate from synaptic vesicles within permeabilized nerve terminals," Neurosci. Lett. 122:179-182.
Naito and Ueda (1985) "Chracterization of Glutamate Uptake into Synaptic Vesicles," J. Neurochem. 44:99-109.
Fykse et al. (1989) "Comparison of the Properties of γ-Aminobutyric Acid and L-Glutamate Uptake into Synaptic Vesicles Isolated from Rat Brain," J. Neurochem. 52:946-951.
Tabb et al. (1992) "Glutamate Transport into Synaptic Vesicles," J. Biol Chem. 267:15412-15418.
Ueda (1986) "Glutamate Transport in the Synaptic Vesicle," in *Excitatory Amino Acids*, Macmillan Press, London, pp 173-195.
Eldred et al. (1994) "Orally Active Non-Peptide Fibrinogen Receptor (GpIIb/IIIa) Antagonists: Identification of 4-[4-[4-(Aminoimino-methyl)phenyl]-l-piperazinyl]-1-piperidineacetic Acid as a Long-Acting, Broad-Spectrum Antithrombotic Agent" J. Med. Chem. 37:3882-3885.
Ku et al. (1995) "Potent Non-peptide Fibrinogen Receptor Antagonists Which Present an Alternative Pharmacophore," J. Med. Chem. 38:9-12.
Pearson and Lipman (1988) "Improved tools for biological sequence comparison," Proc. Natl. Acad. Sci. 85:2444-2448.
Lipman and Pearson (1985) "Rapid and Sensitive Protein Similarity Searches," Science 227:1435-1441.
Carlson et al. (1989) Glutamate Uptake into Synaptic Vesicles: Competitive Inhibition by Bromocriptine, J. Neurochemistry 53:1889-1894.

(Continued)

*Primary Examiner*—Anish Gupta
(74) *Attorney, Agent, or Firm*—Medlen & Carroll, LLP

(57) ABSTRACT

Compositions and methods for treating neurosynaptic disorder in a subject are described. More specifically, compositions and methods for inhibiting glutamate uptake by synaptic vesicles in a subject are set forth. In one embodiment, the composition is inhibitory protein factor (IPF) and the subject is a human.

14 Claims, 16 Drawing Sheets

OTHER PUBLICATIONS

Siegel and Monty (1966) "Determination of Molecular Weights and Frictional Ratios of Proteins in Impure Systems by Use of Gel Filtration and Density Gradient Centrifugation. Application to Crude Preparations of Sulfite and Hydroxylamine Reductases," Biochim.Biophys. Acta 112: 346-362.

Martin and Ames (1961) "A Method for Determining the Sedimentation Behavior of Enzymes: Application to Protein Mixtures," J. Biol. Chem. 236:1372-1379.

Moon and McMahon (1990) "Generation of Diversity in Nonerythroid Spectrins," J. Biol. Chem. 265:4427-4433.

Harris and Morrow "Proteolytic Processing of Human Brain Alpha Spectrin (Fodrin): Identification of a Hypersensitive Site," J. Neuroscience 8:2640-2651.

Harris et al. (1988) "The Calmodulin-binding Site in α-Fodrin Is Near the Calcium-dependent Protease-I Cleavage Site," J. Biol. Chem. 263:15754-15761.

Cheney et al.(1986) "Purification of Fodrin from Mammalian Brain," Meth. Enzymol. 134:42-54.

Rise et al. (1991) "Genes for Epilepsy Mapped in the Mouse," Science 253:669-673.

Kurokawa et al. (1966) "Metabolic Studies on ep Mouse, a Special Strain with Convulsive Predisposition," Prog. Brain Res. 21A 112-130.

Stabach et al. (1997) "Site Directed Mutagenesis of all Spectrin at Codon 1175 Modulates Its μ-Clapain Susceptibility," Biochem. 36:57-65.

Di Stasi et al. (1991) "Neuronal Fodrin Proteolysis Occurs Independently of Excitatory Amino Acid-Induced Neurotoxicity," Neuron 6:445-454.

Fischer-Bovenkerk et al. (1988) "ATP-Dependent Glutamate Uptake into Synaptic Vesicles from Cerebellar Mutant Mice," J. Neurochem. 51:1054-1059.

Harris et al. (1989) "Calmodulin Regulates Fodrin Susceptibility to Cleavage by Calcium-dependent Protease 1" J. Biol. Chem. 264:17401-17408.

Lewis et al. (1997) "Synaptic Vesicle Glutamate Uptake in Epileptic (EL) Mice," Neurochem. Int. 31:581-585.

Martin et al. (1995) "Proteolysis of Fodrin (Non-erythroid Spectrin) during Apoptosis," J. Biol. Chem. 270:6425-6428.

Otswald et al. (1994) "Subcellular Distribution of Calpain and Calpastatin Immunoreactivity and Fodrin Proteolysis in Rabbit Hippocampus After Hypoxia and Glucocorticoid Treatment," J. Neurochem. 63:1069-1076.

Özkan et al. (1997) "A protein factor that inhibits ATP-dependent glutamate and γ-aminobutyric acid accumulation into synaptic vesicles: Purification and initial characterization," Proc. Natl. Acad. Sci. USA 94:4137-4142.

Shioi et al. (1989) "Glutamate uptake into synaptic vesicles of bovine cerebral cortex and electrochemical potential difference of proton across the membrane," Biochem. J. 258:499-504.

Siman et al. (1984) "Brain fodrin: Substrate for calpain I, an endogenous calcium-activated protease," Proc. Natl. Acad. Sci. USA 81:3752-3576.

Siman et al. (1985) "Regulation of glutamate receptor binding by the cytoskeletal protein fodrin," Nature 313:225-228.

Wang et al. (1989) "Calmodulin-binding proteins as calpain substrates," Biochem. J. 262:693-706.

Winter et al. (1993) "Glutamate Uptake System in The Presynaptic Vesicle: Glutamic Acid Analogs as Inhibitors and Alternate Substrates," Neurochem. Res. 18(1):79-85.

GenBank Accession No. U26396.

* cited by examiner

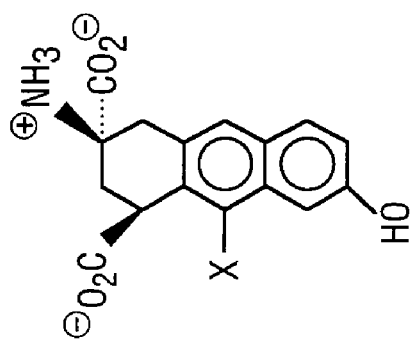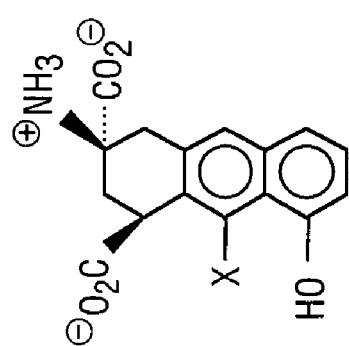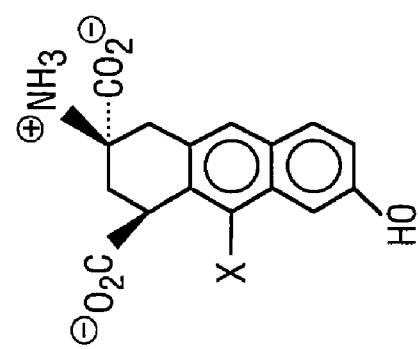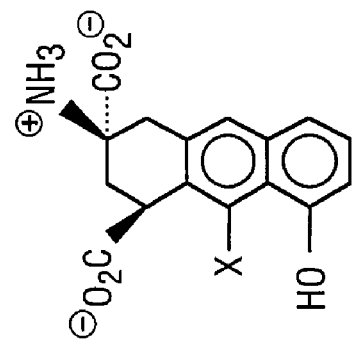
FIG. 1G

```
   1  MDPSGVKVLE  TAEDIQERRQ  QVLDRYHRFK  ELSTLRRQKL  EDSYRFQFFQ  RDAEELEKWI
  61  QEKLQIASDE  NYKDPTNLQG  KLQYHQAFEA  EVQANSGAIV  KLDETGNLMI  SEGHFASETI
 121  RTRLMELHRQ  WELLLEKMRE  KGIKLLQAQN  LVQYLRECED  VMDWINDKEA  IVTSEELGQD
 181  LEHVEVLQKK  FEEFQTDMAA  HEERVNEVNQ  FAAKLIQEQH  PEEELIKTKQ  DEVNAAWQRL
 241  KGLALQRQGK  LFGAAEVQRF  NRDVDETISW  IKEKEQLMAS  DDFGRDLASV  QALLRKHEGL
 301  ERDLAALEDK  VKALCAEADR  LQQSHPLSAT  QIQVKREELI  TNWEQIRTLA  AERHARLNDS
 361  YRLQRFLADF  RDLTSWVTEM  KALINADELA  SDVAGAEALL  DRHQEHKGEI  DAHEDSFKSA
 421  DESDQALLAA  GHYASDEVRE  KLTVLSEERA  ALLELWELRR  QQYEQCMDLQ  LFYRDTEQVD
 481  NWMSKQEAFL  LNEDLGDFLD  SVEALLKKHE  DFEKSLSAQE  EKITALDEFA  TKLIQNNHYA
 541  MEDVATRRDA  LLSRRNALHE  RAMRRRAQLA  DSFHLQQFFR  DSDELKSWVN  EKMKTATDEA
 601  YKDPSNLQGK  VQKHQAFEAE  LSANQSRIDA  LEKAGQKLID  VNHYAKDEVA  ARMNEVISLW
 661  KKLLEATELK  GIKLREANQQ  QQFNRNVEDI  ELWLYEVEGH  LASDDYGKDL  TNVQNLQKKH
 721  ALLEADVAAH  QDRIDGVTIQ  ARQFQDAGHF  DAENIKKKQE  ALVARYEALK  EPMVARKQKI
 781  ADSLRLQQLF  RDVEDEETWI  REKEPIAAST  NRGKDLIGVQ  NLLKKHQALQ  AEIAGHEPRI
 841  KAVTQKGNAM  VEEGHFAAED  VKAKLHELNQ  QRRQDLEDSL  KWEALKAKAS  QAQQYFADAN
 901  EAESWMREKE  PIVGSTDYGK  DEDSAEALLK  KHEALMSDLS  AYGSSIQALR  EQAQSCRQQV
 961  APTDDETGKE  LVLALYDYQE  KSPREVTMKK  GDILLLNST  NKDWWKVEVN  DRQGFVPAAY
1021  VKKLDPAQSA  SRENLLEEQG  SIALRQEQID  NQTRITKEAG  SVSLRMKQVE  ELYHSLLELG
1081  EKRXGMLEKS  CKKFMLFREA  NELQQWINEK  ADLEQVEVLQ  KKFDDFQKDL  PWKSARLMVH
1141  KANESRLKDI  NKVAEDLESE  GLMAEEVQAV  QQQEVYGMMP  RDETDSKTAS  PWKSARLMVH
```

FIG. 6A

```
   1                    YHRFK ELSTLRRQKL EDSYRFQFFQ RDAEELEKWI
  36 QEKLQIASDE NYKDPTNLQG KLQKHQAFEA EVQANSGAIV KLDETGNLMI SEGHFASETI
  96 RTRLMELHRQ WELLLEKMRE KGIKLLQAQN LVQYLRECED VMDWINDKEA IVTSEELGQD
 156 LEHVEVLQKK FEEFQTDMAA HEERVNEVNQ FAAKLIQEQH PEEELIKTKQ DEVNAAWQRL
 216 KGLALQRQGK LFGAAEVQRF NRDVDETISW IKEKEQLMAS DDFGRDLASV QALLRKHEGL
 276 ERDLAALEDK VKALCAEADR LQQSHPLSAT QIQVKREELI TNWEQIRTLA AERHARLNDS
 336 YRLQRFLADF RDLTSWVTEM KALINADELA SDVAGAEALL DRHQEHKGEI DAHEDSFKSA
 396 DESGQALLAA GHYASDEVRE KLTVLSEERA ALLELWELRR QQYEQCMDLQ LFYRDTEQVD
 456 NWMSKQEAFL LNEDLGDFLD SVEALLKKHE DFEKSLSAQE EKITALDEFA TKLIQNNHYA
 516 MEDVATRRDA LLSRRNALHE RAMRRRAQLA DSFHLQQFFR DSDELKSWVN EKMKTATDEA
 576 YKDPSNLQGK VQKHQAFEAE LSANQSRIDA LEKAGQKLID VNHYAKDEVA ARMNEVISLW
 636 KKLLEATELK GIKLREANQQ QQFNRNVEDI ELWLYEVEGH LASDDYGKDL TNVQNLQKKH
 696 ALLEADVAAH QDRIDGVTIQ ARQFQDAGHF DAENIKKQE ALVARYEALK EPMVARKQKL
 756 ADSLRLQQLF RDVEDEETWI REKEPIAAST NRGKDLIGVQ NLLKKHQALQ AEIAGHEPRI
 816 KAVTQKGNAM VEEGHFAAED VKAKLHELNQ KWEALKAKAS QRRQDLEDSL QAQQYFADAN
 876 EAESWMREKE PIVGSTDYGK DEDSAEALLK KHEALMSDLS AYGSSIQALR EQAQSCRQQV
 936 APTDDETGKE LVLALYDYQE KSPREVTMKK GDILTLLNST NKDWWKVEVN DRQGFVPAAY
 996 VKKLDPAQSA SRENLLEEQG SIALRQEQID NQTRITKEAG SVSLRMKQVE ELYHSLLELG
1056 EKRKGMLEKS CKKFMLFREA NELQQWINEK EAALTSEEVG ADLEQVEVLQ KKFDDFQKDL
1116 KANESRLKDI NKVAEDLESE GLMAEEVQAV QQQEVY
```

FIG. 6B

COMPOSITIONS AND METHODS FOR THE INHIBITION OF NEUROTRANSMITTER UPTAKE OF SYNAPTIC VESICLES

This is a Divisional of application Ser. No. 08/840,006 filed on Apr. 15, 1997, now U.S. Pat. No. 6,127,520.

This invention was made with government support under Javits Neuroscience Investigator Award NS 26884 awarded by the National Institutes of Health, Department of Health and Human Services. The Government has certain rights in the invention.

FIELD OF THE INVENTION

The present invention pertains to compositions and methods for the inhibition of neurotransmitter uptake of synaptic vesicles.

BACKGROUND

Glutamate is now widely accepted as the major excitatory neurotransmitter in the central nervous system of all vertebrates [see e.g., Nakanishi (1992) *Science* 258, 597–603]. Abnormalities in glutamatergic synaptic transmission have been implicated in many neuropathologies, including certain seizures, ischemia-induced neuronal death, schizophrenia, Alzheimer's disease, Parkinson's disease, and Huntington's disease [see e.g., Coyle and Puttfarcken (1993) *Science* 262, 689–695].

Excessive release of glutamate into the synaptic cleft is believed to be a common underlying basis for many of these disease states. There is also evidence that some glutamate receptors such as the NMDA (N-methyl-D-aspartate) and the metabotropic receptors may be involved in neuronal plasticity [see e.g., Bashir et al. (1993) *Nature* 363, 347–350].

Evidence which has been accumulated for the last decade strongly supports the notion that glutamatergic neurotransmission occurs via an exocytotic process involving the interaction of glutamate-containing synaptic vesicles with the plasma membrane of the presynaptic ending. In support of this is the observation that glutamate is taken up into purified, isolated synaptic vesicles in an ATP-dependent manner [see e.g., Naito and Ueda (1983) *J. Biol. Chem.* 258, 696–699; and Tabb and Ueda (1991) *J. Neurosci.* 11, 1822–1828], consistent with immunocytochemical evidence that glutamate is concentrated in synaptic vesicles which are distinct from GABA-vesicles [Storm-Mathisen et al. (1983) *Nature* 301, 517–520].

Biochemical evidence also suggested that high concentrations of glutamate are accumulated in brain synaptic vesicles in vivo. Studies by Nicholls and co-workers indicate that the exocytotic pool of glutamate originates from a noncytoplasmic site within the nerve terminal [see e.g., Nicholls and Sihra (1986) *Nature* 321, 772–773; and McMahon and Nicholls (1991) *Biochim. Biophys. Acta* 1059, 243–264].

Moreover, Kish and Ueda [(1991) *Neurosci. Lett.* 122, 179–182] provided evidence that vesicular glutamate is released in a calcium-dependent manner from permeabilized synaptosomes. This body of evidence clearly demonstrates that synaptic vesicles are the storage site of the glutamate to be released from nerve terminals.

The vesicular glutamate uptake system has several distinctive properties which distinguish it from the cellular glutamate re-uptake system present in the plasma membrane. It is stringently specific for glutamate, has a relatively high $K_m$, and requires low concentrations of chloride for optimal activity [(Naito and Ueda (1985) *J. Neurochem.* 44, 99–109; and Fykse et al. (1989) *J. Neurochem.* 52, 946–951].

The driving force for glutamate uptake is provided by an electrochemical proton gradient generated by a V-type $H^+$-ATPase in the synaptic vesicle membrane [Naito and Ueda (1985) *J. Neurochem.* 44, 99–109]. The precise mechanism by which the glutamate transporter utilizes this proton gradient to drive glutamate uptake is not fully understood; however, compounds that interfere with the formation of such gradients have a marked inhibitory effect on glutamate transport [Naito and Ueda (1985) *J. Neurochem.* 44, 99–109; Tabb et al. (1992) *J. Biol Chem* 267, 15412–15418].

It has been proposed that glutamate uptake into synaptic vesicles represents the critical step in diverting glutamate away from the metabolic pathway and toward the neurotransmitter pathway [Ueda (1986) in *Excitatory Amino Acids* (Roberts P. J., Storm-Mathisen J., and Bradford H. F., eds), pp. 173–195, Macmillan Press, London]. Thus, it is desirable to regulate the vesicular glutamate uptake system under normal physiological conditions. Alterations in such a regulatory system could cause the abnormalities in glutamatergic neurotransmission implicated in the variety of central nervous system disorders mentioned above. However, while many studies have focused on changes associated with postsynaptic glutamate receptors, few have addressed presynaptic regulation of glutamatergic neurotransmission at the level of vesicular transport. What is needed are compositions and methods for regulating the uptake of glutamate into the synaptic vesicles.

SUMMARY OF THE INVENTION

The invention provides compositions and methods for the inhibition of neurotransmitter uptake of synaptic vesicles. In one embodiment, the present invention provides compositions and methods for regulating the uptake of glutamate by synaptic vesicles. In one embodiment, the present invention contemplates the inhibition of glutamate uptake by synaptic vesicles with an inhibitor. In one embodiment, the inhibitor is a peptide, and in a preferred embodiment, the peptide is inhibitory protein factor (IPF).

The term "IPF" is used in reference to three proteins (IPF αβγ) each having an apparent molecular weight on electrophoresis gels of between 130 and 138 kD. IPF can be purified from animal brain tissue, including human tissue.

In one embodiment, the present invention contemplates a composition comprising a purified fragment of fodrin having glutamate uptake inhibition activity, said fragment having an N-terminus and a C-terminus. The composition is not limited by the exact amino acid sequence, however in one embodiment the N-terminus of the fragment corresponds to $Tyr^{26}$ of fodrin (that is to say, the N-terminus of the fragment begins with this amino acid and has additional amino acids that follow after this initial amino acid in the sequence order found in intact fodrin—although it is not intended to be limited to any precise length). In another embodiment, the purified fragment comprises a peptide having the amino acid sequence (SEQ ID NO:1) EAALTSEEVG within 150 amino acids of the C-terminus of the peptide, more preferably, within 130 amino acids of the C-terminus of the peptide, and most preferably, within 120 amino acids of the C-terminus of the peptide.

Likewise, the present invention is not limited by the precise size of the fragment of fodrin. In one embodiment, the purified fragment comprises IPF α, while in other embodiments the composition comprises a purified fragment of IPF α. In yet other embodiments, the purified fragment comprises IPF β or IPF γ.

While the present invention is not limited to a specific amino acid sequence, in one embodiment the present invention contemplates a composition comprising a purified peptide having glutamate uptake inhibition activity with an N-terminus sequence comprising the amino acids (SEQ ID NO:2) YHRFK (i.e., the peptide N-terminus begins with this sequence and has at least these amino acids in this order). In another embodiment, the said purified peptide has an N-terminus comprising the amino acids (SEQ ID NO:3) YHRFKELSTL (i.e., the peptide N-terminus begins with this sequence and has at least these amino acids in this order). In yet another embodiment, the purified peptide has an N-terminus comprising the amino acids (SEQ ID NO:4) YHRFKELSTLRRQKLEDSYR (i.e., the peptide N-terminus begins with this sequence and has at least these amino acids in this order).

The present invention also contemplates a method of isolating a glutamate uptake inhibitor, comprising: a) providing an animal brain; and b) subjecting said animal brain to a purification procedure such that a purified fodrin fragment having glutamate uptake inhibition activity is produced. The present invention is not limited by the specific purified fragment. In certain embodiments the purified fragment comprises IPF α, IPF β or IPF γ.

The present invention contemplates screening assays for candidate compounds. While the present invention is not limited by any particular screening assay, in one embodiment, the present invention contemplates a method for testing compounds for their ability to overcome or offset the synaptic vesicle glutamate uptake inhibition activity of the fodrin fragments of the present invention. In one embodiment, the screening method comprises a) providing: i) synaptic vesicles, ii) as purified fodrin fragment having glutamate uptake inhibition activity, and iii) candidate compound; and b) combining said candidate compound with said synaptic vesicles and said fragment such that the effect of said candidate compound on glutamate uptake by said synaptic vesicles can be assessed. The method is not limited by the purified fragment utilized, in certain embodiments the purified fragment comprises IPF α, IPF β or IPF γ.

Another screening assay contemplated by the present invention contemplates a method for testing compounds for their ability to overcome or offset the synaptic vesicle glutamate uptake inhibition activity of fragments of IPF. In one embodiment, the method comprises a) providing: i) synaptic vesicles, ii) a purified fragment of IPF having synaptic vesicle glutamate uptake inhibition activity, and iii) candidate compound; and b) combining said candidate compound with said synaptic vesicles and said purified fragment such that the effect of said candidate compound on said fragment's effect on glutamate uptake by said synaptic vesicles can be assessed. The assay is not limited by the nature of the purified fragments, however in certain embodiments the purified fragment comprises fragments of IPF α, IPF β or IPF γ.

The present invention also contemplates screening method of testing candidate compound for inhibition of calpain cleavage of fodrin, comprising: a) providing: i) fodrin, ii) calpain, and iii) candidate compound; and b) combining said candidate compound with said fodrin and said calpain such that the effect of said candidate compound on calpain cleavage of fodrin can be assessed. In one embodiment, antibodies to fodrin are used as control inhibitors of calpain digestion.

In yet another embodiment, the present invention contemplates a screening method of testing candidate compound for inhibition of trypsin cleavage of IPF, comprising: a) providing: i) trypsin, ii) purified IPF, and iii) candidate compound; and b) combining said candidate compound with said trypsin and said IPF such that the effect of said candidate compound on cleavage of said IPF by said trypsin can be assessed. In one embodiment, antibodies to IPF a fragments are used as control inhibitors of trypsin cleavage. The screening method is not limited by the nature of the purified IPF utilized. In certain embodiments, the purified fragment comprises IPF α, IPF β or IPF γ.

The present invention also contemplates antibodies to fodrin and purified fragments of fodrin. While the present invention is not limited by the sequence of the epitope of the purified fragment, in one embodiment the epitope sequence corresponds to a portion of a decapeptide from fodrin. In yet another embodiment the antibodies have been passed through a column containing purified fodrin. In still another embodiment, the antibodies will bind to a purified fragment of fodrin, but do not bind to fodrin.

The present invention also contemplates immobilized fodrin and fragments, such as fragments bound to a resin. The present invention is not limited by the specific nature of the purified fragment bound. In certain embodiments the purified fragment comprises IPF α, IPF β or IPF γ. In yet another embodiment, the purified fragment comprises a fragment of IPF α.

DESCRIPTION OF THE DRAWINGS

FIG. 6A compares partial IPF α sequence (SEQ ID NO:5) with the sequence of human α fodrin, while FIG. 6B shows the predicted sequence (SEQ ID NO:6) of IPF α based upon the C-terminus being commensurate with the calpain cleavage site for fodrin and the N-terminus beginning at amino acid 26 of fodrin.

DEFINITIONS

Figure 1A:
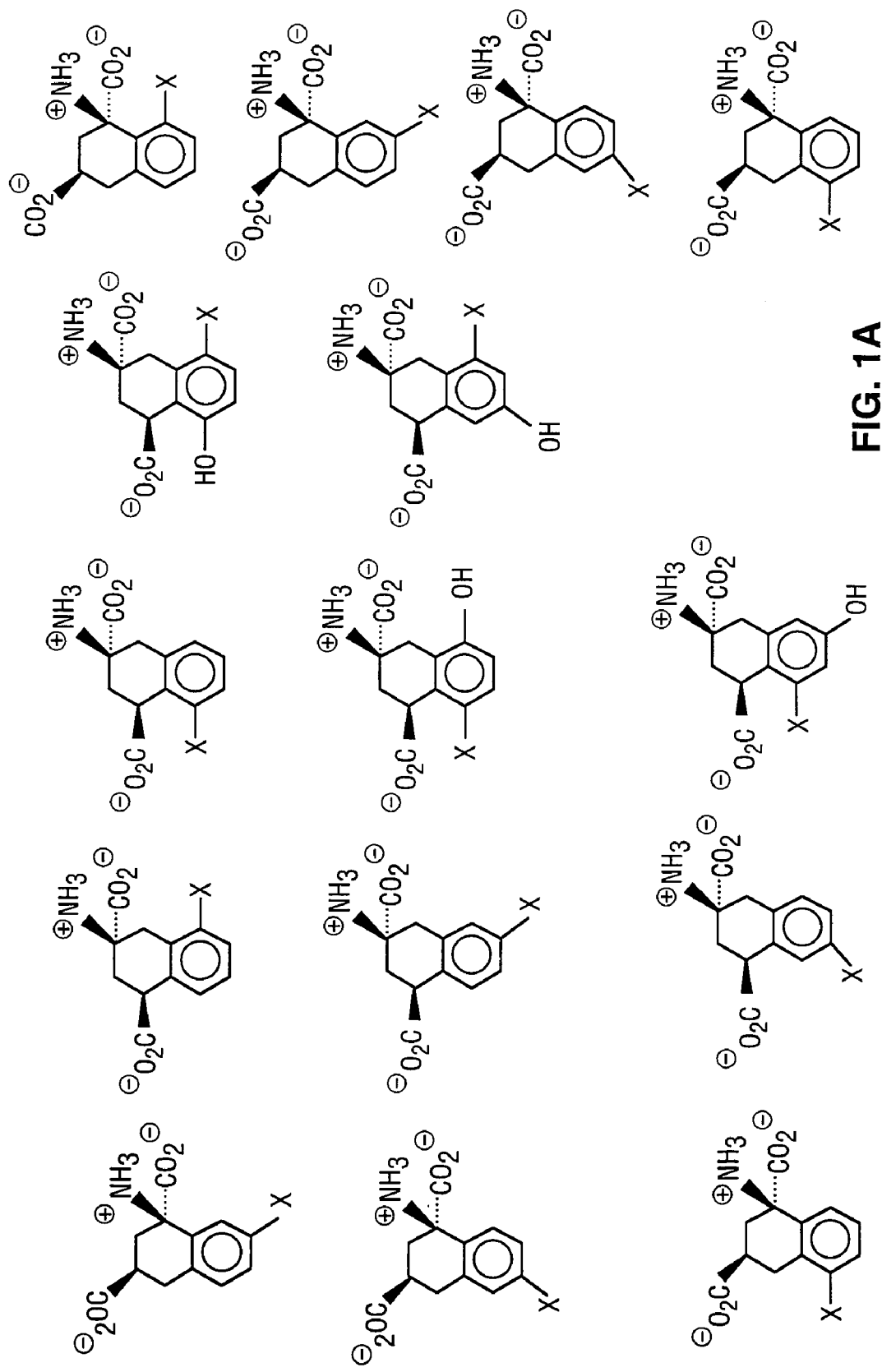
FIG. 1 depicts a series of halogenated glutamic acid analogs useful for inhibiting synaptic vesicle glutamate uptake.
Figure 1B:
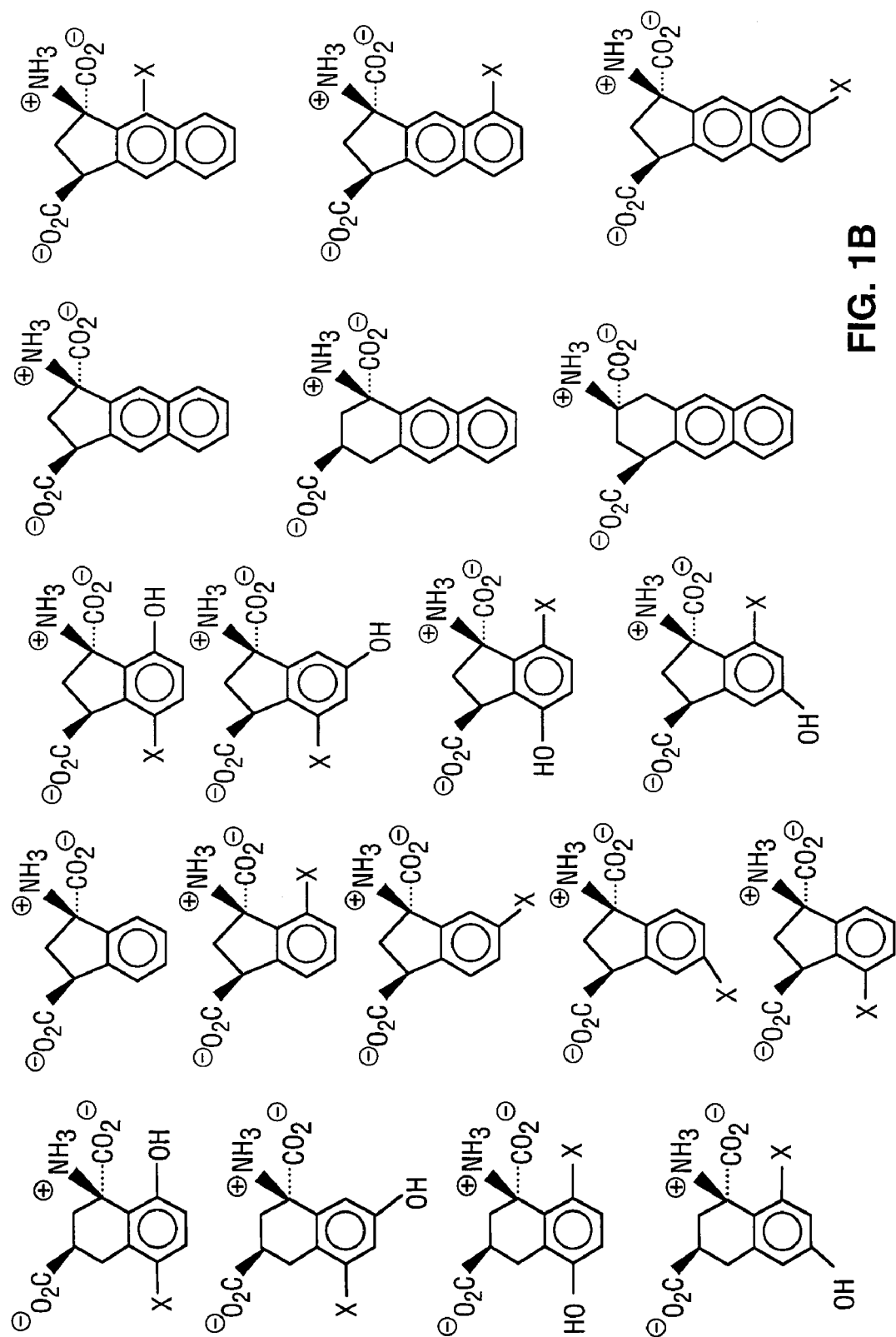
Figure 1C:
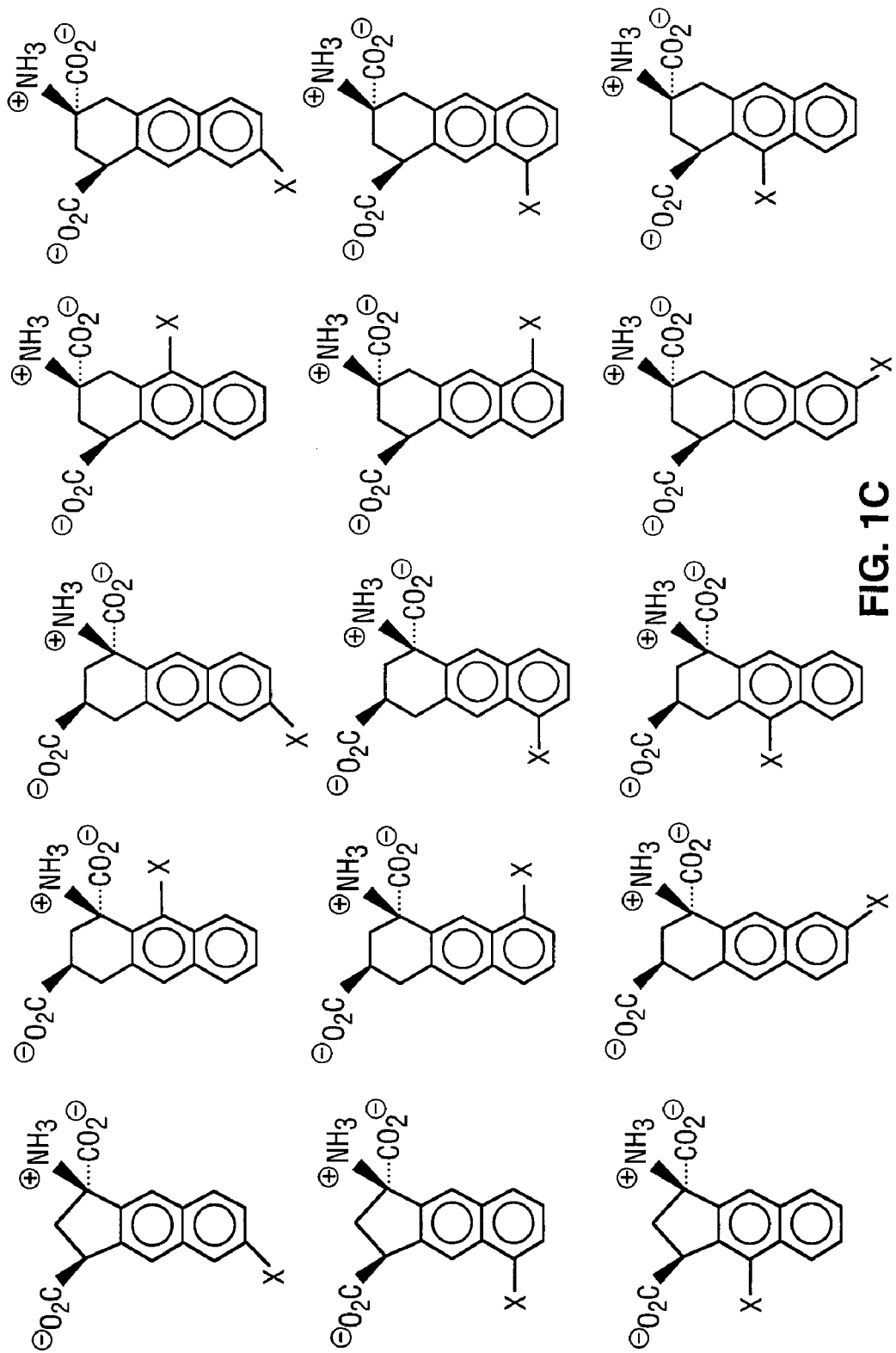
Figure 1D:
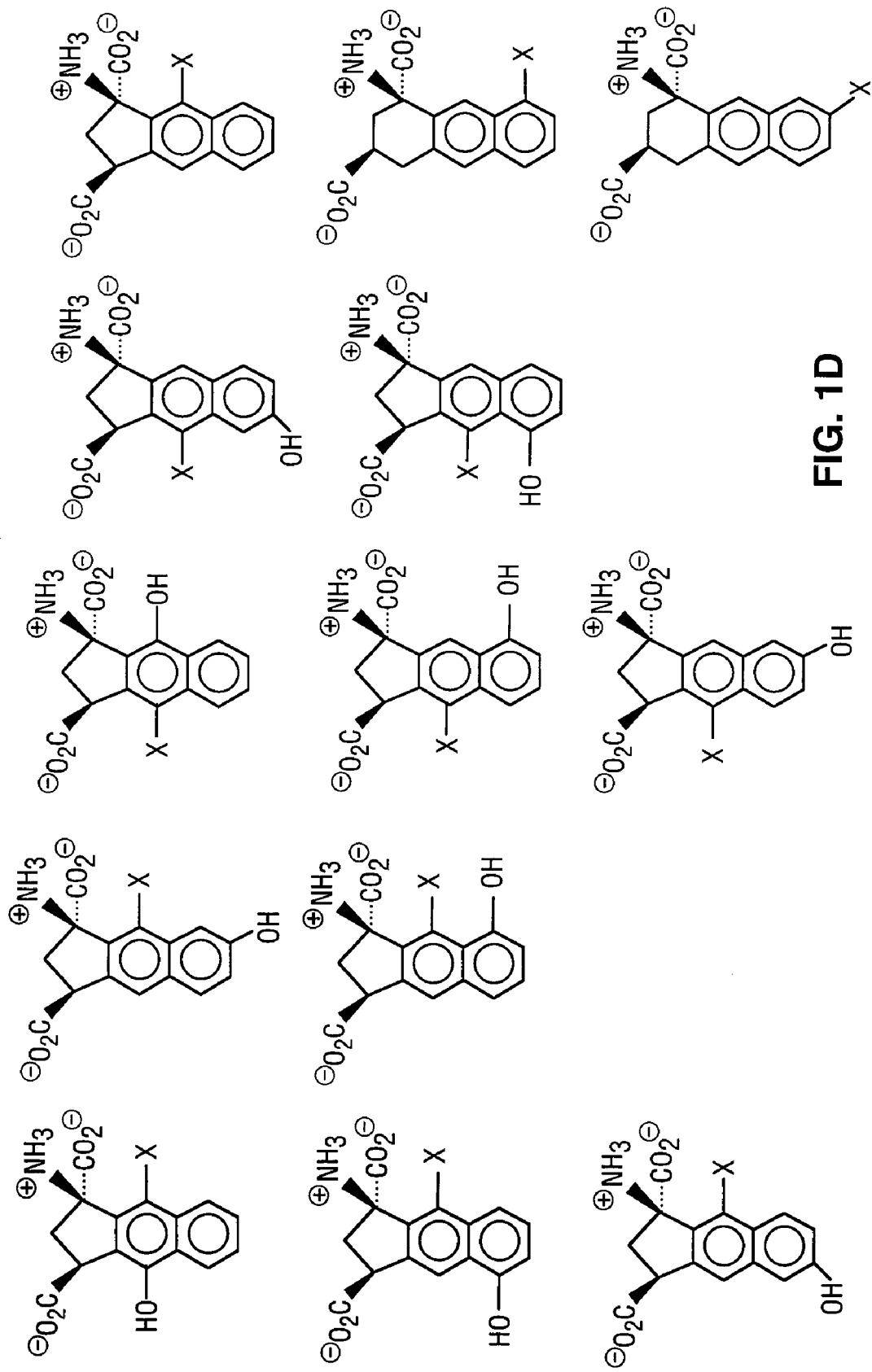
Figure 1E:
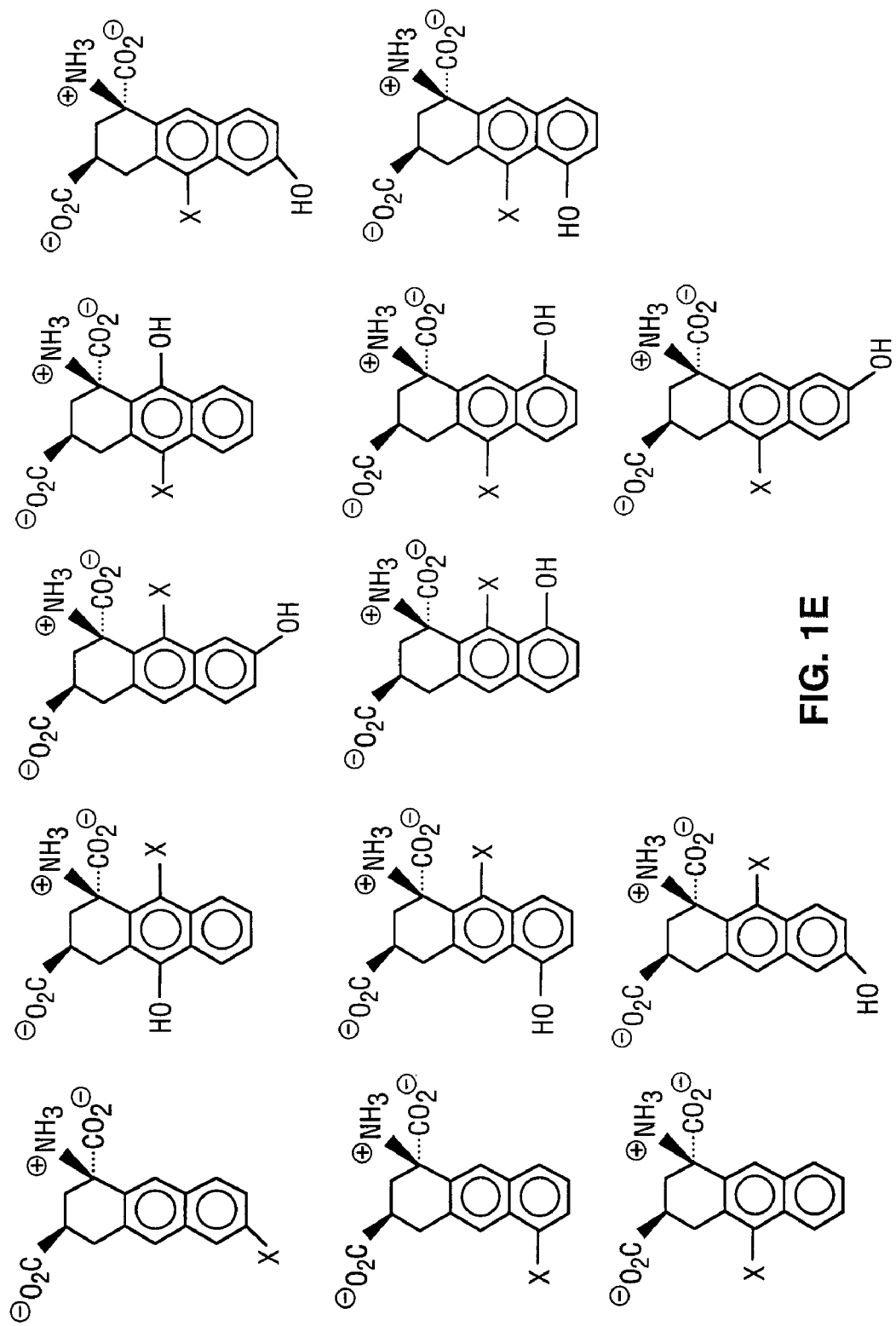
Figure 1F:
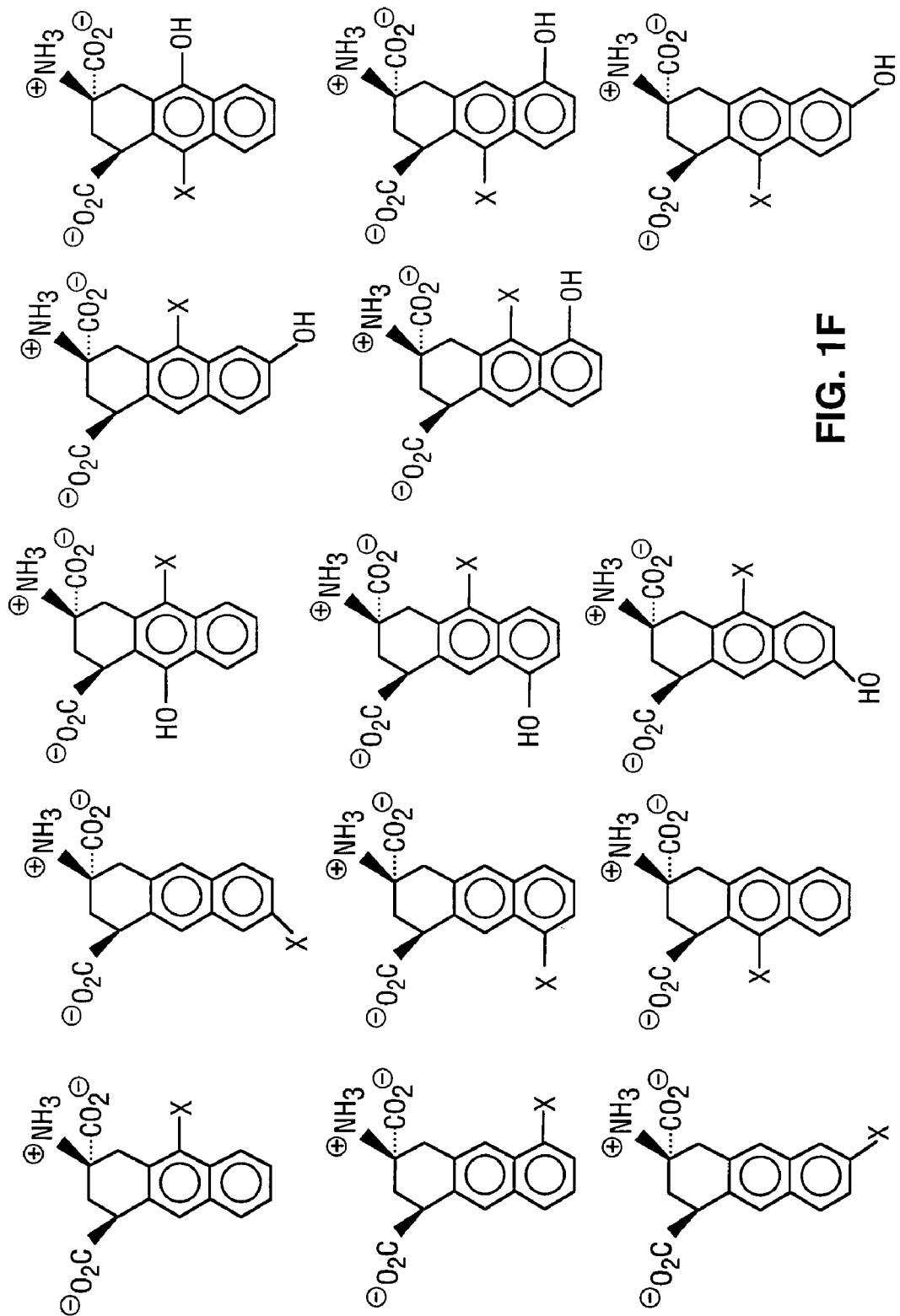

"Glutamate uptake inhibition activity" as used herein refers to the property of inhibiting the uptake of glutamate by synaptic vesicles. A "glutamate uptake inhibitor" is a peptide that demonstrates glutamate uptake inhibition activity.

"IPF" as used herein refers to a peptide derived from animal brain tissue that is a glutamate uptake inhibitor. IPF is a designation for three similar peptides "IPF $\alpha\beta\gamma$."

"Neurosynaptic disorder" as used herein refers to undesirable neuronal activity resulting in seizures of a subject or damage to a subject's neural tissue. Examples of such conditions include, but are not limited to, epileptic seizures, Huntington's Disease, Alzheimer's Disease, etc.

"GABA" as used herein refers to $\gamma$-aminobutyric acid and acts as an inhibitory transmitter in the central nervous system.

"Fodrin" as used herein refers to a protein of a family of proteins that bundle and crosslink actin filaments. Actin filaments are a part of the cytoskeleton and are responsible for maintaining cell structure and integrity. Fodrin is a rod-shaped protein that lines the cortical cytoplasm of neurons. Fodrin can be identified as a high molecular weight protein present in brain membranes by i) comigration on NaDodSO$_4$ polyacrylamide gels with purified fodrin, ii) reactivity with antibodies to purified fodrin, and iii) a proteolytic map following calpain activation comparable to that found after calpain mediated degradation of pure fodrin. "$\alpha$ fodrin" as used herein refers to the fodrin as isolated from human cells. "Fodrin fragment" as used herein refers to a peptide or protein whose amino acid sequence is equivalent to a portion of the amino acid sequence of fodrin. "Purified fodrin fragment" as used herein refers to a fodrin fragment that is isolated from the natural environment of fodrin or a fodrin fragment created by degradation of fodrin that has been isolated from its natural environment.

"Calpain" as used herein refers to a calcium calmodulin dependent neutral proteinase isolated from the cytostolic fractions of various animal tissues or cells with a molecular weight of 94–100 kDa by gel filtration on Sephacryl 300.

"Trypsin" as used herein refers to a proteolytic enzyme from pancreatic juice that hydrolyses polypeptides on the carboxyl side of arginine and lysine residues.

"Trypsin sensitive" as used herein refers to a peptide with an arginine or lysine residue that is sensitive to cleavage by trypsin on the carboxyl side.

"Purified" as used herein refers to a composition wherein at least one component has been removed from the crude extract causing the proportion of protein of interest (e.g., IPF or fodrin) to be increased relative to the total proteins found in a crude extract.

"Apparent molecular weight" as used herein refers to the estimated molecular weight as determined by methods (e.g., gel electrophoresis, sucrose gradient, gel filtration) and compared to the molecular weights of standards run by the same method.

"True molecular weight" as used herein refers to the molecular weight of a peptide as determined by the additive molecular weights of its component amino acids as determined by complete sequencing of the peptide.

DETAILED DESCRIPTION OF THE INVENTION

The present invention pertains to compositions and methods for the inhibition of neurotransmitter uptake of synaptic vesicles. In a preferred embodiment, the inhibitor is IPF. In another embodiment, the inhibitor is a product of exposure of IPF to trypsin.

IPF is isolated from brain tissue and refers to three distinct proteins with relative molecular weights of 138,000 ($\alpha$), 135,000 ($\beta$), and 132,000 ($\gamma$), respectively. It has been determined that IPF is best purified from brain material excised from young animals as opposed to mature animals.

While an understanding of the precise mechanism is not necessary to carry out the present invention, it is believed that IPF interacts with a synaptic vesicle-specific protein that leads to a blockade of neurotransmitter storage by an indirect mechanism. The physiological role of IPF remains to be elucidated. The fact that IPF seems to derive from $\alpha$ fodrin is particularly intriguing since fodrin purified from whole brain is itself devoid of inhibitory activity (data not shown). Regardless of the mechanism of action of IPF, it is a potent, endogenous inhibitor of vesicular neurotransmitter uptake.

The present invention also contemplates degradation products of IPF that exhibit synaptic vesicle glutamate uptake inhibition and the use thereof. While the present invention is not limited by the type or method of producing these degradation products, in one embodiment IPF is degraded with trypsin and these degradation products inhibit glutamate uptake by synaptic vesicles.

Mimetics

Compounds mimicking the necessary conformation for recognition and docking to the receptor binding to the peptides of the present invention are contemplated as within the scope of this invention. For example, mimetics of IPF peptides are contemplated. A variety of designs for such mimetics are possible. For example, cyclic IPF-containing peptides, in which the necessary conformation for binding is stabilized by nonpeptides, are specifically contemplated. U.S. Pat. No. 5,192,746 to Lobl et al, U.S. Pat. No. 5,169,862 to Burke, Jr., et al, U.S. Pat. No. 5,539,085 to Bischoff et al, U.S. Pat. No. 5,576,423 to Aversa et al, U.S. Pat. No. 5,051,448 to Shashoua, and U.S. Pat. No. 5,559,103 to Gaeta et al, all hereby incorporated by reference, describe multiple methods for creating such compounds.

Synthesis of nonpeptide compounds that mimic peptide sequences is also known in the art. Eldred et al, (J. Med. Chem. 37:3882 (1994)) describe nonpeptide antagonists that mimic the Arg-Gly-Asp sequence. Likewise, Ku et al, (J. Med. Chem. 38:9 (1995)) give further elucidation of the synthesis of a series of such compounds. Such nonpeptide compounds that mimic IPF peptides are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the above-described IPF peptides. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic polypeptides useful in glutamate uptake inhibition by synaptic vesicles are those peptides with statistically significant sequence homology and similarity (Z value of Lipman and Pearson algorithm in Monte Carlo analysis exceeding 6).

Glutamate Analogs as Inhibitors of Glutamate Uptake in Synaptic Vesicles

The present invention contemplates the use of glutamate analogs to inhibit glutamate uptake by synaptic vesicles. While not being limited by the nature of the glutamate analogs, halogenated analogs of glutamic acid and cyclic analogs of glutamate are contemplated.

While the present invention is not limited by the type of halogenated glutamic acid analog utilized, examples of such compounds are set forth in FIG. 1. Where the structures set forth signify an X substituent, any of the halogens (i.e., fluorine, chlorine, bromine or iodine) may be used.

For cyclic analogs of glutamate, it is contemplated that compounds that have a three-dimensional charge distribution identical or very close to that of (1S,3R)-1-aminocylcopentane-1,3-dicarboxylate (ACPD), an analog of L-glutamate, are useful. Preferably, the compound has a hydrophobic moiety similar to that seen in (1S,3R)-ACPD. Examples include, but are not limited to, 1-aminocylcobutane-1,3-dicarboxylic acid, 1-aminocylcohexane-1,3-dicarboxylic acid and 1-aminocylcoheptane-1,3-dicarboxylic acid [all available commercially from Tocris-Cookson, Bristol, UK]. The present invention is not limited by the form of the cyclic analog of glutamate. For example, derivatives of cyclic analogs (e.g., halogenated, methylated or ethylated) are also contemplated.

Drug Screening Assays

The present invention contemplates in vitro screening assays for the discovery of 1) new glutamate uptake inhibitors, 2) compounds that can overcome glutamate uptake inhibition, 3) inhibitors of calpain degradation of fodrin, 4) inhibitors of trypsin degradation of IPF and 5) compounds that can overcome glutamate uptake inhibitor by the trypsin degradation products of IPF. The present invention also contemplates in vivo screening assays to assess efficacy.

These screening assays are described in detail below. Glutamate and synaptic vesicles are utilized in the in vitro assays. The present invention is not limited by the nature of the synaptic vesicles utilized. For example, synaptic vesicles from bovine and mice [as set forth in Examples below] and from rats [Carlson et al. (1989) *J. Neurochemistry* 53 1889–1894], as well as other sources are contemplated.

1. New Glutamate Uptake Inhibitors

The present invention contemplates the use of IPF with glutamate and synaptic vesicles to assess glutamate uptake inhibition of other candidate inhibitors. While the present invention is not limited by the actual assay protocol, IPF can be used as a standard for testing the inhibition properties of other candidate compounds.

In such an assay, glutamate uptake inhibition by synaptic vesicles is assessed as set forth in the Examples below. Such uptake can be measured with and without the presence of IPF. Meanwhile, candidate inhibitor can be assayed under similar conditions in the absence of IPF. The extent of glutamate uptake by the synaptic vesicles in the presence of candidate inhibitor can then be compared to uptake with no additive and uptake in the presence of IPF. If uptake in the presence of candidate inhibitor reduces glutamate uptake by synaptic vesicles as compared to uptake in the absence of candidate inhibitor, the candidate inhibitor is considered to exhibit glutamate uptake inhibition activity.

2. Compounds That Overcome Glutamate Uptake Inhibition

The present invention contemplates the screening of compounds useful for overcoming inhibition of glutamate uptake by synaptic vesicles. While the present invention is not limited by the actual assay protocol, it is contemplated that candidate compounds can be screened for their ability to overcome IPF inhibition of glutamate uptake by synaptic vesicles.

In such an assay, glutamate uptake by synaptic vesicles is inhibited by IPF as set forth in the Examples below. Candidate compound can be added and uptake by synaptic vesicles can be assessed. If glutamate uptake by synaptic vesicles in the presence of IPF and candidate compound is increased in relation to uptake in the presence of IPF alone, the candidate compound overcomes glutamate uptake inhibition activity by synaptic vesicle glutamate uptake inhibitors.

3. Inhibitors of Calpain Degradation of Fodrin

It is believed that the C-terminus of IPF corresponds with a calpain cleavage site of fodrin. It is therefore hypothesized that the C-terminus region of IPF can be formed from fodrin by cleavage with calpain. This cleavage should result in a fragment of fodrin of about 150 kD, with a C-terminus matching that of IPF and an N-terminus similar to that of fodrin. This fragment is in contrast to IPF itself of about 138 kD, whose N-terminus corresponds with the amino acid sequence of fodrin beginning at position 26 (i.e., lacking the first 25 amino acids of fodrin).

The present invention contemplates the screening of compounds useful for inhibiting calpain cleavage of fodrin. While the present invention is not limited by the actual assay protocol, it is contemplated that candidate compounds can be screened for their ability to inhibit calpain cleavage of fodrin by introducing candidate compound with fodrin and calpain, and assessing the presence and nature of any cleavage products (e.g., by examining the products on gel electrophoresis).

In such an assay, if the cleavage products in the presence of candidate compound do not correspond with the 150 kD or 138 kD proteins described above, the candidate compounds is useful as a inhibitor of fodrin cleavage by calpain.

4. Inhibitors of Trypsin Degradation of IPF

As set forth in the Examples below, it has been determined that trypsin can cleave IPF. These degradation products have synaptic vesicle glutamate uptake inhibition activity similar to that of IPF itself.

The present invention contemplates the screening of compounds useful for inhibiting trypsin degradation of IPF. While the present invention is not limited by the actual assay protocol, it is contemplated that candidate compounds can be screened for their ability to inhibit trypsin cleavage of IPF by introducing candidate compound with IPF and trypsin, and assessing the presence and nature of any cleavage products.

In such an assay, if the cleavage products in the presence of candidate compound do not correspond with the trypsin cleavage products described above, the candidate compounds is useful as a inhibitor of IPF cleavage by trypsin.

5. Overcoming Glutamate Uptake Inhibition by IPF Fragments

As described above, fragments of IPF exhibit synaptic vesicle glutamate uptake inhibition activity. While the present invention is not limited by the nature of the fragments, the present invention does contemplate the screening of compounds useful for overcoming such IPF fragment inhibition of glutamate uptake by synaptic vesicles.

In such an assay, glutamate uptake by synaptic vesicles is inhibited by IPF fragments as set forth in the Examples below. Candidate compound can be added and uptake by synaptic vesicles can be assessed. If glutamate uptake by synaptic vesicles in the presence of IPF fragments and candidate compound is increased in relation to uptake in the presence of IPF fragments alone, the candidate compound overcomes glutamate uptake inhibition activity by IPF fragments.

6. In Vivo Assays of Glutamate Uptake Inhibitors

The present invention contemplates the treatment of synaptic disorder in subjects and is not limited by the type of glutamate uptake inhibitor utilized. Candidate inhibitors may be tested prior to administration to a patient. Once drugs possessing inhibitory activity and lacking neuronal toxicity are identified, they may be administered according to the invention to a patient exhibiting symptoms of a disease or disorder associated with neuronal injury or death, particularly to patients in which neuronal injury or death is a result of glutamate toxicity. Preferred inhibitors are those which are capable of crossing the blood/brain barrier.

The above-identified inhibitors and also drugs identified according to the invention as inhibitors of glutamate uptake by synaptic vesicles can be tested in animals for their effectiveness in inhibiting or preventing neuronal seizures and injury and/or death. Conventional animal testing systems are well-known in the art. Each animal may be injected with a range of doses of the drug and the toxicity or lack of toxicity of the drug may be assessed by the survival rate of the animals. Animals which exhibit symptoms of neuronal injury, or animals subject to conditions generating cerebral infarction (i.e., stroke), e.g, oxygen or glucose deprived animals, can then be tested. The effects of the drug on peripheral tissues can be assessed by histological examination of the tissues. Based on these in vivo tests, the overall effectiveness of the drug can be determined, and an effective dose and mode of administration can also be determined. The present invention is not limited by the nature of the animal or disease modeled. In one embodiment, the animal model is of a type as set forth in the Examples below (e.g., the EL mouse strain).

Drug Therapy and Formulations

The present invention is not limited by the method of administration of the inhibitor. In one embodiment, it is by conventional means available for use in conjunction with pharmaceuticals; either in combination with one another or in combination with other therapeutic agents. It is contemplated that the methods of the present invention be administered alone or can be administered with a pharmaceutical carrier selected on the basis of the chosen route of administration and standard pharmaceutical practice. In one embodiment, the inhibitor is administered by a implanting device for the release of neuroinhibitory compounds. One example of such a device is described in U.S. Pat. No. 5,573,528 to Aebischer et al., herein incorporated by reference.

In one preferred embodiment, the inhibitor is administered orally in solid dosage forms, such as capsules, tablets, or powders, or in liquid dosage forms, such as elixirs, syrups, and suspensions; however, it can also be administered parenterally, in sterile liquid dosage forms, or rectally in the form of suppositories.

One skilled in the art will be capable of adjusting the administered dose depending upon known factors such as the mode and route of administration; age, health, and weight of the recipient; nature and extent of symptoms, kind of concurrent treatment, frequency of treatment, and the effect desired. In one embodiment, the dosage is increased to overcome a non-responsive condition.

Additionally, the inhibitor can be employed in admixture with conventional excipient, i.e., pharmaceutically acceptable organic or inorganic carrier substances suitable for parenteral (e.g., topical application) or enteral (e.g., oral) which do not deleteriously react with the active compounds.

Suitable pharmaceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, stabilizers, wetting agents, emulsifier, salts for influencing osmotic pressure, buffers, coloring, flavoring, and/or aromatic substances and the like which do no deleteriously react with the active compounds. They can also be combined where desired with other agents, e.g. vitamins.

Additionally, the inhibitor may be introduced in a polymer gel for controlled release. Methods of producing such gels are set forth in U.S. Pat. No. 5,567,435 to Hubbel et al., herein incorporated by reference. Methods of injecting polymers are set forth in U.S. Pat. No. 5,567,612 to Vacanti et al., hereby incorporated by reference. Moreover, in cases where the inhibitor chosen is a peptide, methods for incorporating peptides into polymers is described in U.S. Pat. No. 5,482,996 to Russell et al., herein incorporated by reference.

For enteral application, particularly suitable are tablets, liquids, drops, suppositories, or capsules. A syrup, elixir, or the like can be used wherein a sweetened vehicle is employed. Sustained or directed release compositions can be formulated, e.g., liposomes or those wherein the active compound is protected with differentially degradable coating, e.g., by microencapsulation, multiple coatings, etc.

In this manner, the present invention may be introduced into a subject in polymeric microspheres for the controlled release of the compound. Methods of producing microspheres from polymer can be found in U.S. Pat. No. 5,601,844 to Kagayama et al. and U.S. Pat. Nos. 5,529,914 and 5,573,934 to Hubbel et al., herein incorporated by reference.

For parenteral application, particularly suitable are injectable, sterile solutions, preferably oily or aqueous solutions, as well as suspensions, emulsions, or implants including suppositories. Nebulizers and inhalation aerosols may also be used. Ampules are in convenient unit dosages. It is also possible to freeze-dry the new compounds and use the lyophilizates obtained, for example, for the preparation of products for injection.

For other parenteral applications, such as topical applications and non-sprayable forms, viscous to semi-solid or solid forms comprising a carrier compatible with topical application and having a dynamic viscosity preferably greater than water. Suitable formulations include but are not limited to transdermal patches, solutions, suspensions, emulsions, creams, ointments, powders, liniments, salves, aerosols, etc., which are, if desired, sterilized or mixed with auxiliary agents, e.g., preservations, stabilizers, wetting agents, buffers, or salts for influencing osmotic pressure, etc.

Also suitable for topical application are sprayable aerosol preparations wherein the inhibitor, preferably in combination with a solid or liquid inert carrier material, is packaged in a squeeze bottle or in admixture with pressurized volatile, normally gaseous propellant, e.g., a freon. The application of these embodiments can be to the skin or mucous membrane or in the interior of the body and can be oral, peroral, enteral, pulmonary, rectal, nasal, vaginal, lingual, intervenous, intraarterial, intracardial, intramuscular, intraperitoneal, intracutaneous, subcutaneous. The parenteral preparations are preferably sterile or sterilized products.

In this manner, U.S. Pat. No. 4,895,727 to Allen, herein incorporated by reference, describes a method of inducing a reservoir effect in skin and mucous membranes so as to enhance penetration and retention and reduce transdermal flux of topically applied therapeutic and cosmetic pharmacologically active agents. U.S. Pat. No. 4,557,934 to Cooper, herein incorporated by reference, describes topical pharmaceutical compositions containing a pharmaceutically-active agent and the penetration enhancing agent, 1-dodecylazacycloheptan-2-one. This composition provides marked transepidermal and percutaneous delivery of the selected pharmaceutically-active agent.

Suppositories containing inhibitor can be created using a suitable oleaginous or water-soluble base. The oleaginous class includes cocoa butter and fats with similar properties: the water-soluble class includes polyethylene glycols.

Other medicaments containing inhibitor can be produced in a known manner, whereby the known and customary pharmaceutical adjuvants as well as other customary carrier and diluting agents can be used. Examples include, but are not limited to, gelatins, natural sugars such as sucrose or lactose, lecithin, pectin, starch (for example cornstarch), alginic acid, tylose, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, methyl cellulose, cellulose phthalate, stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane).

Other adjuvants can also be substances which bring about decomposition (so-called explosives) such as: cross-linked polyvinyl pyrrolidone, sodium carboxy methyl starch, sodium carboxy methyl cellulose or microcrystalline cellulose. Likewise, known coating agents such as e.g. polyacrylates, cellulose ethers and the like can be used.

For the production of solutions, there can be used water of physiologically compatible organic solvents, as for example, ethanol, 1,2-propylene glycol, polyglycols, e.g., diethylene glycol, triethylene glycol and dipropylene glycol and their derivatives dimethyl sulfoxide, fatty alcohols, e.g., stearyl alcohol, cetyl alcohol, lauryl alcohol and oleyl alcohol, triglycerides, e.g. glyceryl olelate glyceryl stearate, glyceryl palmitate, and glyceryl acetate, partial esters of glycerine, e.g., glyceryl monostearate, glyceryl distearate, glyceryl monopalmitate, paraffins, and the like.

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, polyethylene oxide condensation products of fatty alcohols, alkyl phenolene or fatty acids or also 1-methyl-3-(2-hydroxyethyl)imidazolidone-(2). The term polyoxyethylated means in this context that the substances in question contain polyoxyethylene chains whose polymerization is generally between 2 to 40 and especially between 10 to 20.

Such polyoxyethylated substances can be obtained, for example, by reacting compounds containing hydroxyl groups (e.g. mono or diglycerides or unsaturated compounds such as, e.g., those containing the oleic acid residues) with ethylene oxide (e.g. 40 moles ethylene oxide per mole glyceride). Examples of oleotriglycerides are olive oil, peanut oil, castor oil, sesame oil, cotton seed oil and corn oil. [See also Fiedler, *Lexicon der Hilfastoffe fur Pharmazie, Kosmetik and angrezende Gebiete* [Lexicon of Adjuvants for Pharmacy, Cosmetics an Related Areas] pp. 191–195 (1971)].

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium-meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

EXAMPLES

The following examples serve to illustrate certain preferred embodiments and aspects of the present invention and are not to be construed as limiting the scope thereof.

In the following examples, the following abbreviations apply: IPF, inhibitory protein factor; BSA, bovine serum albumin; EDTA, (ethylenedinitrilo)-tetraacetic acid; GABA, γ-aminobutyric acid; HEPES, 4-(2 hydroxyethyl)-1-piperazine-ethanesulfonic acid; PAE, polyethyleneimine; PMSF, phenylmethyl sulfonyl fluoride; SDS-PAGE, sodium dodecyl sulfate polyacrylamide gel electrophoresis; V-type $H^+$-ATPase, vacuolar-type proton translocating ATPase.

In the following examples, the materials utilized were obtained as follows: Polyethyleneimine (PAE)-1000 anion-exchanger was purchased from Amicon Corporation. Hydroxylapatite HPT was from Bio-Rad. Superdex S200 26/60 and Mono Q 5/5 columns were purchased from Pharmacia. [$^3$H]Glutamate (50 Ci/mmol) was purchased from Amersham Corporation. CytoScint ES scintillation fluid was from ICN. Whatman GFC filters were purchased from VWR. Ammonium sulfate was from Mallinckrodt. Protein was quantified with the Coomassie Protein Assay Kit from Pierce, using bovine serum albumin as standard. All other chemicals and chromatography media were purchased from Sigma.

Example 1

Purification and Use of IPF

In this example, the purification and use of an inhibitor of synaptic glutamate uptake is described. The example is divided into three sections: A) preparation of the synaptic vesicles and synaptosomes, B) purification of inhibitory protein factor (IPF), and C) inhibition of glutamate uptake by synaptic vesicles with IPF. All of the following procedures were performed on ice or in a 4° C. cold-room unless otherwise noted.

A. Preparation of Synaptic Vesicles and Synaptosomes

Bovine synaptic vesicles were prepared by a slight modification of the procedure described by Tabb et al. [(1992) *J. Biol. Chem.* 267, 15412–15418]. Briefly, bovine brains were obtained from the local slaughterhouse. On ice, the meninges were removed form each brain, the cerebral cortex dissected, and excess white matter removed. About 300 grams of cortex were briefly blended in 600 ml of 0.32 M sucrose, 1 mM NaHCO$_3$, 1 mM magnesium acetate, 0.5 mM calcium acetate, 0.2 mM phenylmethylsulfonyl fluoride (solution A) in a Waring blender with 3×7 second bursts; solution A was used in all steps unless noted otherwise.

The homogenate was diluted to two liters in solution A and was rehomogenized in a 300-ml tight fitting Teflon-glass homogenizer (Kontes, Vineland, N.J.) with two strokes, at 1900 rpm. Each batch was diluted to 3 liters and was centrifuged in a Sorvall GSA rotor at 2500 rpm for 10 minutes. The supernatant (S1) was saved, and the pellets (P1) from various batches were pooled, diluted to 4 liters, rehomogenized and recentrifuged at 2500 rpm for ten minutes. This supernatant (S1) was pooled with the previous S1 and was centrifuged in a GSA rotor at 13,000 rpm for 15 minutes. This pellet was saved, and the supernatant was discarded.

The P2 was resuspended in solution A to 1.6 liters. This suspension was diluted with an equal volume of 1.28 M sucrose, to make the final concentration of sucrose 0.8 M, and was then centrifuged at 13,000 rpm in a GSA rotor for 45 minutes. The floating myelin bands and supernatant were aspirated, and the pellets (synaptosomes) were saved. The synaptosomes were resuspended in two liters of ice-cold lysing buffer (6 mM Tris-maleate, pH 8.1), diluted to 8 liters lysing buffer, mechanically stirred at 4° C. for 45 minutes and were then centrifuged at 19,000 rpm in a Sorvall SS-34 rotor for 15 minutes. The supernatant was then concentrated from 8 liters to 800 ml in an Amicon spiral ultraconcentrator, equipped with an S1Y30 cartridge (30,000 molecular weight cutoff). The retentate was then centrifuged at 43,000 rpm in a Beckman 45Ti rotor ultracentrifuge rotor for 70 minutes.

The pellets (crude synaptic vesicles) were resuspended in 20 ml of lysing buffer and were layered over six discontinuous sucrose gradients (12 ml 0.4 M, 6 ml 0.6 M), and were then centrifuged at 35,000 rpm in a Beckman Type 45Ti rotor for two hours. The lysing buffer and 0.4 M sucrose layers (but not the 0.4 M, 0.6 M sucrose interface; it contains plasma membrane contaminants) were removed, diluted with lysing buffer and were centrifuged at 47,000 rpm in a Beckman Ti50 rotor for 60 minutes. The pellets were saved and were either resuspended in solution B (0.32 M sucrose, 1 mM NaHCO$_3$, 1 mM dithiothreitol) at about 5 mg/ml and stored in liquid nitrogen and were stable for at least one month.

Bovine synaptosomes used in FIG. 5 (see description below) were collected during the preparation of synaptic vesicles [Tabb et al. (1992) *J. Biol. Chem.* 267, 15412–15418]. Synaptosomes were resuspended in normal Krebs-Ringers (0.15 M NaCl, 6.2 mM KCl, 1.2 mM Na$_2$HPO$_4$, 1.2 mM MgSO$_4$, 10 mM glucose, 20 mM Tris-HEPES, pH 7.4) or low Na$^+$ Krebs-Ringers (substituting 0.15 M choline chloride for NaCl) prior to assay.

B. Purification of IPF 25 calf brains were obtained fresh from a local slaughterhouse, and the cerebellum, brain stem, and excess white matter removed to yield 5,500–6,000 grams of cerebral tissue. A Waring blender was used to mince 300 grams of cortex at a time in 800 ml of 1 mM PMSF, 1 mM EDTA, 5 mM 2-mercaptoethanol, 6 mM Tris-HCl, pH 8.3 (lysing buffer). The blended material was then diluted to ~40 liters in lysing buffer and homogenized to smoothness by passing through a large, continuous-flow homogenizer. The entire suspension was then centrifuged at 13,000 rpm (27,300 g$_{max}$) for 15 min in a Sorvall GSA rotor. The resulting supernatant (~25 liters) was concentrated to 10 liters in an Amicon spiral ultra-concentrator equipped with a S1Y30 cartridge (30,000 molecular weight cut-off) prior to further fractionation.

The inhibitory protein factor was purified to apparent homogeneity as follows:

Step 1: Ammonium sulfate precipitation—The crude cellular extract (~10 liters) was adjusted to 45% saturation with ammonium sulfate and incubated for 30 min. The precipitate was collected by centrifugation for 15 min at 13,000 rpm (27,300 g$_{max}$), resuspended to 2.5 liters in lysing buffer and dialyzed overnight against 55 liters of same. The dialyzed sample was then clarified by centrifuging for 70 min at 45,000 rpm (235,400 g$_{max}$) in a Beckman Type 45Ti rotor. The resulting supernatant (2.6 liters, 24,000 mg protein) was generally stored overnight at −20° C. prior to anion-exchange chromatography.

Step 2: Anion-exchange chromatography—One half of the 45% ammonium sulfate precipitate at a time (~1.3 liters) was loaded onto a PAE-1000 column (7.5 cm×32 cm) equilibrated with lysing buffer, at a flow-rate of 50 ml/min. After collection of the flow-through fraction, bound protein was eluted with 2 liters each of 0.2, 0.5, and 1.0 M NaCl dissolved in the column buffer. The 0.5 M NaCl eluate (1.5 liters) was dialyzed overnight against 58 liters of a solution containing 1 mM MgCl$_2$, 0.2 mM PMSF, and 10 mM Tris-maleate, pH 8.0 (HAP column buffer). The 0.5 M NaCl eluate was usually fractionated on hydroxylapatite immediately following dialysis.

Step 3: Hydroxylapatite column chromatography—This step was typically run twice, with each run utilizing one of the two 0.5 M NaCl eluates obtained from the PAE-1000 column. The dialyzed PAE 0.5 M eluate (1.6 liters, 3,500 mg protein) was applied to a hydroxylapatite column (7.5 cm×9 cm) equilibrated with HAP column buffer at a flow-rate of 20 ml/min. Bound protein was eluted with increasing steps of potassium phosphate (0.01, 0.05, 0.1, and 1 M) dissolved in HAP column buffer. The 0.05 M eluate was collected and later combined with the same fraction obtained from the second column run. The combined HAP 0.05 M eluates were adjusted to 80% saturation with ammonium sulfate, and the precipitates collected and resuspended to 200 ml in a solution containing 1 mM EDTA, 0.2 mM PMSF, and 10 mM Tris-maleate, pH 7.0 (yellow column buffer). This was dialyzed overnight against two 18-liter changes of the same.

Step 4: Reactive Yellow-86 chromatography—The dialyzed 0.05 M phosphate eluate from the hydroxylapatite column (250 ml, 1,800 mg protein) was loaded onto a Reactive Yellow-86 agarose column (4.5 cm×22 cm) equilibrated with yellow column buffer. Approximately 95% of loaded protein does not bind to the column and is collected in the flow-through. Bound protein is eluted with successive steps of 0.06, 0.3, and 1 M NaCl dissolved in column buffer, at a flow-rate of 14 ml/min. The 0.3 M NaCl eluate (250 ml, 60 mg protein) was adjusted to 80% saturation with ammonium sulfate and the precipitate collected as previously described. The precipitate was resuspended to 10 ml in yellow column buffer and dialyzed overnight against two 5-liter changes of the same.

Step 5: Gel filtration on Superdex S200—The dialyzed Yellow-86 0.3 M NaCl eluate (10 ml, 18–20 mg protein) was applied to a Superdex S-200 26/60 column (62 cm×65 cm) equilibrated with a solution containing 75 mM KCl, 1 mM EDTA, 0.2 mM PMSF, and 10 mM Tris-maleate, pH 7.0. The column was run at 1 ml/min, and 6 ml fractions collected (60 total). Typically, fractions 23–30 were pooled, and an 80% ammonium sulfate precipitate collected as previously described. Precipitate was resuspended in 2 ml of a solution containing 1 mM EDTA, 0.2 mM PMSF, and 10 mM Tris-maleate, pH 7.0, and dialyzed against 4 liters of the same for 4 hours just prior to sucrose gradient centrifugation.

The estimated Stokes radius was determined by utilizing plots of $(-\log K_{av})^{1/2}$ vs. the Stokes radius of standard proteins (ferritin, 79 Å; BSA, 35 Å; and myoglobin, 17 Å) according to [Siegel and Monty (1966) *Biochim. Biophys. Acta* 112, 346–362].

Step 6: Sucrose density gradient centrifugation—The dialyzed, ammonium sulfate precipitate from the Superdex S-200 column (2.5 ml, 20–25 mg protein) was layered onto two 36 ml 5–20% sucrose gradients developed in a solution containing 50 mM NaCl, 1 mM EDTA, 0.2 mM PMSF, and 10 mM HEPES, pH 7.4. Gradients were centrifuged for 43 hr at 28,000 rpm (140,000×g$_{max}$) in a Beckman SW28 rotor. A gradient containing catalase (11.3 S), BSA (4.3 S), and myoglobin (2.1 S) was also run in parallel in order to determine the sedimentation coefficients in Table II below [Martin and Ames (1960) *J. Biol. Chem.* 236, 1372–1379]. Typically, thirty-six 1-ml fractions were collected from each gradient by puncturing the tube bottoms.

Step 7: HPLC anion-exchange chromatography—Peak inhibitory fractions from the sucrose gradients (typically fractions 22–26, ~2 mg protein) were pooled and applied to a Pharmacia Mono Q 5/5 anion-exchange column equilibrated with a solution containing 75 mM NaCl, 1 mM EDTA, 0.2 mM PMSF, and 20 mM Tris-HCl, pH 7.6. Bound protein was eluted with a linear NaCl gradient (75–538 mM) developed over 60 min at a flow-rate of 1 ml/min. Fractions were collected (60×1 ml), and 10-µl aliquots were assayed for inhibitory activity. Controls were performed by assaying aliquots from an identical gradient run in the absence of added protein.

Typical results of the procedure used to purify IPF α and IPF β are shown in Table I and in FIGS. 2 and 3 (described below). Hydroxylapatite chromatography at pH 8.0 in the presence of Mg$^{2+}$ proved to be a critical step during purification. Under these conditions, about 50% of the inhibitory activity was found in the 0.05 M phosphate eluate and resolved from a second peak of inhibitory activity present in the 0.1 M eluate. This accounted for the 50% loss of total inhibitory activity seen at this step. The activity in 0.1 M eluate correlated with a 73 kDa protein which may represent a proteolytic digestion product of IPF (EDÖ and TU, unpublished observation).

The dye Reactive Yellow 86 was found to have a particularly selective affinity for IPF. The 0.3 M NaCl eluate from this column provided the first glimpse of the IPF αβγ triplet against the protein background (FIG. 2, lane 6, described below). Greater than 90% of the loaded protein did not bind to this column and, although the column effluent contained the majority of the inhibitory activity, no increase in specific activity was achieved.

Sucrose gradient centrifugation proved effective in the purification of IPF because of the anomalous sedimentation behavior of the IPF triplet. IPF α,β, and γ all migrated identically in 5–20% sucrose gradients, with an apparent sedimentation coefficient of 4.3 S. This step usually yielded at least one fraction that was essentially a purified preparation of IPF αβγ.

These steps and their resulting levels of purification are summarized in Table I, indicating a 1,160-fold to 1,280-fold purification for IPF α and IPF β respectively.

of the inhibitory activity eluted between gradient fractions 24 and 35. Samples for SDS-PAGE were dissociated and electrophoresed. Gel staining was with Coomassie Brilliant Blue.

Figure 2:
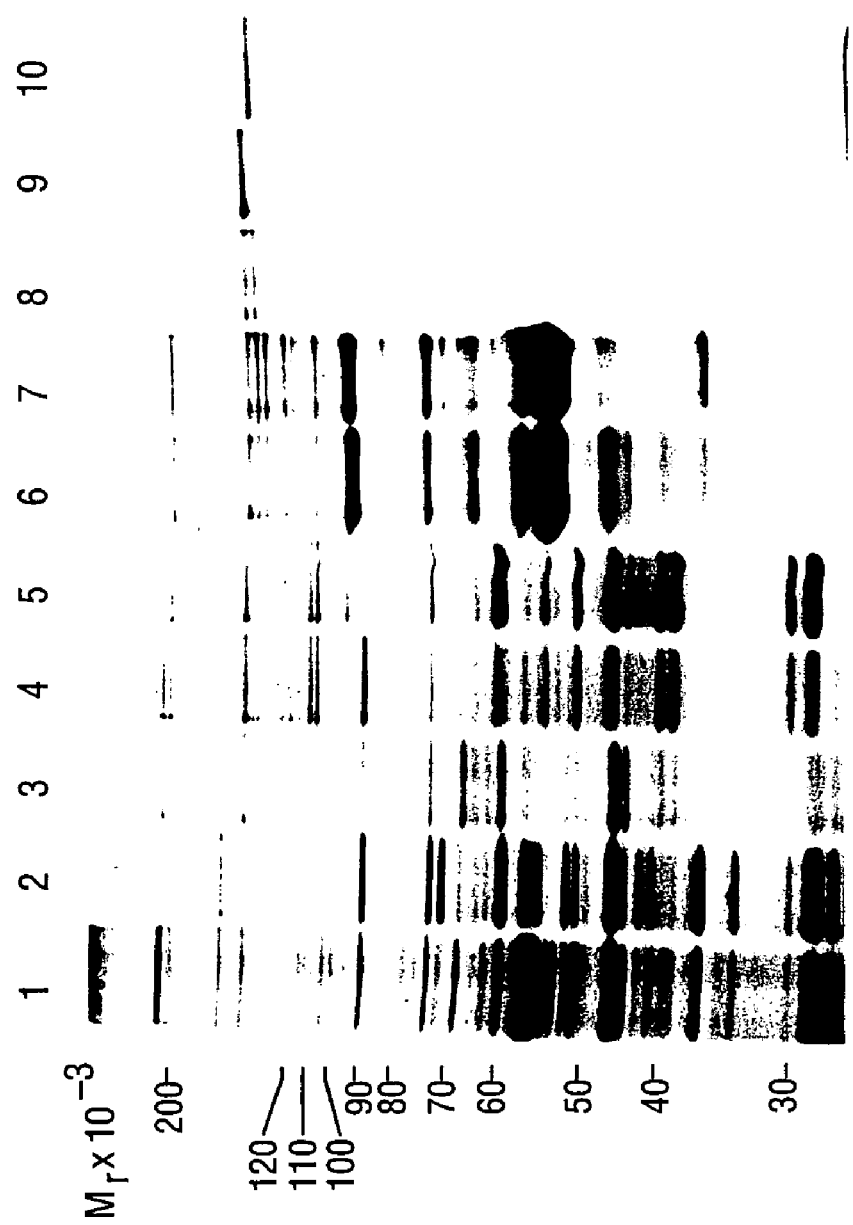
FIG. 2 depicts the SDS-PAGE profiles of fractions obtained during the purification of IPF.
Figure 3:
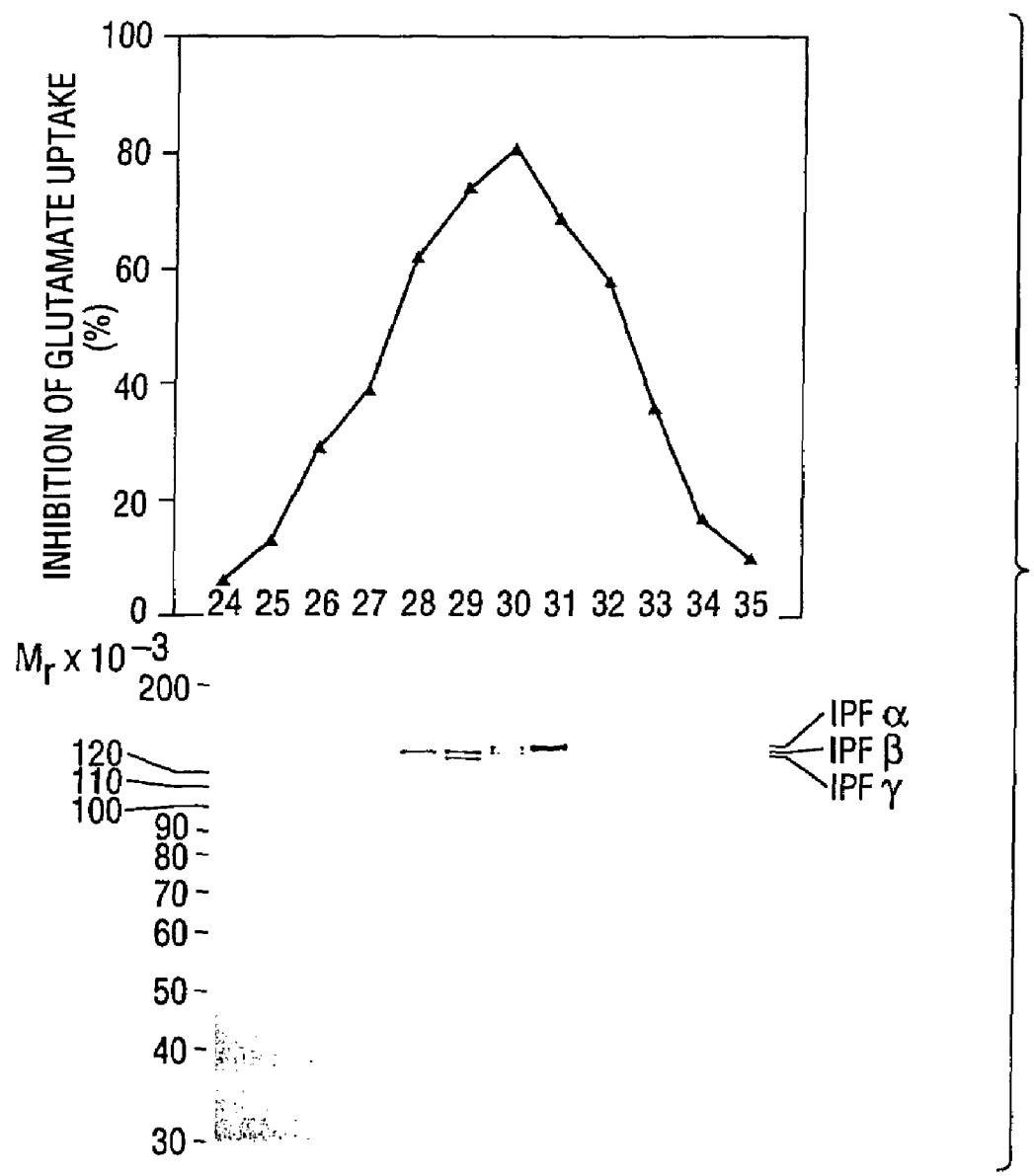
FIG. 3 compares the SDS-PAGE profile (lower panel) of peak inhibitory fractions as eluted from Mono Q HPLC (upper panel).

FIG. 3 shows that high resolution anion-exchange chromatography can partially resolve IPF αβγ into individual components based on assumed differences in net negative charge. It can also be concluded from this figure that both IPF α and IPF β possess inhibitory activity. Fraction 30 (see FIG. 2) usually contained a mixture of IPF α,β and γ, reminiscent of the starting material, while fraction 29 usually contained roughly equal amounts of IPF β and γ. Fraction 28 contained very pure IPF β (135 kDa), and later fractions contained pure IPF α (138 kD).

C. Inhibition of Glutamate Uptake By Synaptic Vesicles

The uptake of [$^3$H]-glutamate into synaptic vesicles was assayed using a modification of the filtration procedure described in [Kish and Ueda (1989) *Meth. Enzymol.* 174,

TABLE I

Purification of IPF from calf brain cytosol.

| Fraction | Total Protein (mg) | IC$_{50}$ (mg/.12 ml) | Total Activity (U) | Yield (%) | Specific Activity (U/mg) | Purificat. (–fold) |
|---|---|---|---|---|---|---|
| Cytosol | 69,960 | 0.50 | 139,920 | 100 | 2 | 1 |
| 45% AS | 26,920 | 0.25 | 107,680 | 77 | 4 | 2 |
| PAE 0.5M | 6,952 | 0.081 | 85,827 | 61 | 12 | 6 |
| HAP 0.05M | 1,824 | 0.040 | 45,600 | 33 | 25 | 13 |
| Yellow 0.3M | 58 | 0.011 | 5,273 | 3.8 | 91 | 46 |
| Superdex Peak | 23 | 0.0050 | 4,600 | 3.3 | 200 | 100 |
| Sucrose Peak | 2.5 | 0.0011 | 2,273 | 1.6 | 909 | 455 |
| Mono Q IPF α | 0.25 | 0.00043 | 581 | 0.42 | 2,326 | 1,160 |
| Mono Q IPF β | 0.25 | 0.00039 | 641 | 0.46 | 2,564 | 1,280 |

FIG. 2 displays SDS-PAGE profiles of the products in the steps of the purification procedure. The starting material and fractions containing the peak inhibitory activity from the various purification steps were dissociated by boiling for 2 min in the presence of 1% SDS, 5% 2-mercaptoethanol, 10% glycerol, and 63 mM Tris-HCl, pH 6.8, and subjected to electrophoresis on a 7.5% SDS-polyacrylamide gel. Gel staining was with Coomassie Brilliant Blue. Lane 1, 40 µg calf-brain homogenate; lane 2, 40 µg crude cytosol; lane 3, 40 µg 45% ammonium sulfate precipitate; lane 4, 40 µg PAE 0.5 M NaCl eluate; lane 5, 40 µg HAP 0.05 M phosphate eluate; lane 6, 40 µg Yellow 86 0.3 M NaCl eluate; lane 7, 20 µg gel filtration peak; lane 8, 5 µg sucrose gradient peak; lane 9, 1.5 µg Mono Q-purified IPF α; lane 10, 1.5 µg Mono Q-purified IPF β.

FIG. 3 compares the SDS-PAGE profile, (upper panel), of peak inhibitory fractions as eluted from Mono Q HPLC, (lower panel). Peak inhibitory fractions from two 5–20% sucrose density gradients (12 ml, 2 mg protein) were applied to a Mono Q 5/5 anion-exchange column equilibrated in 75 mM NaCl, 1 mM EDTA, 0.2 mM PMSF, 20 mM Tris-HCl, pH 7.6. Bound protein was eluted in sixty 1-ml fractions by a linear NaCl gradient (75–538 mM) developed over 60 min. Aliquots of 10 µl were assayed for inhibitory activity (upper panel) and for composition by SDS-PAGE (lower panel). All 9–25]. Briefly, synaptic vesicles (30–50 µg protein) were suspended in 120 µl of an incubation medium consisting of 0.23 M sucrose, 4 mM KCl, 4 mM MgSO$_4$, 2 mM aspartate, 10 mM methionine sulfoximine, 1 mM spermine, ±2 mM ATP, ±IPF sample 10 mM HEPES, pH 7.4, and 50 µM [$^3$H]glutamate (specific activity, 0.017 Ci/mmol). Glutamate uptake was initiated by transferring the mixtures from ice to a 30° C. water bath, and the uptake reaction was allowed to proceed for 10 min. Baseline ATP-dependent glutamate uptake activity was calculated as the glutamate taken up in the presence of ATP minus that taken up in the absence of ATP. Throughout this work, glutamate uptake activity refers to the ATP-dependent portion, which was typically greater than 90% of the total. One unit (U) of the inhibitory protein factor was defined as the amount of protein required to inhibit 50% of ATP-dependent glutamate uptake over a period of 10 min at 30° C.

Figure 4:
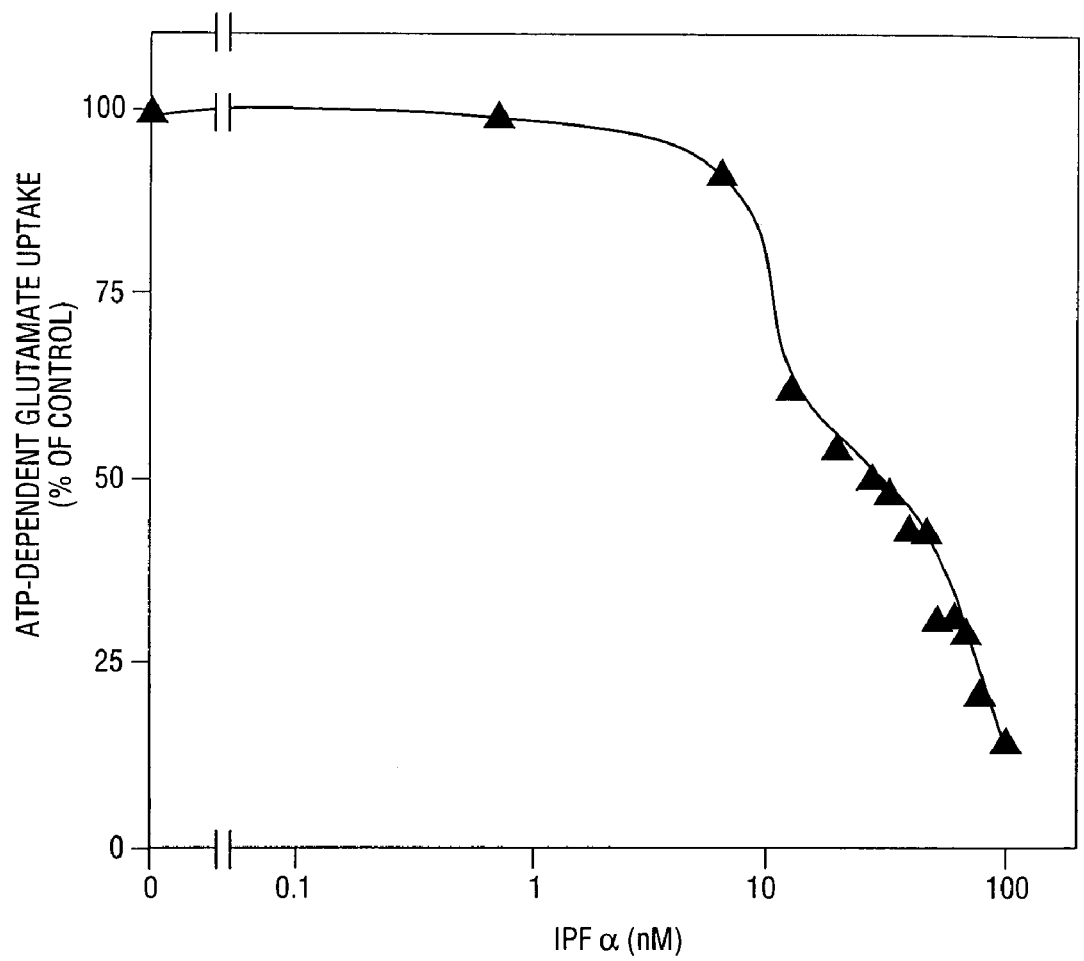
FIG. 4 depicts a dose-response curve for purified IPF α. As the concentration of IPF is increased, the ATP-dependent glutamate uptake is decreased.

FIG. 4 shows that IPF α is a potent inhibitor of ATP-dependent glutamate uptake in synaptic vesicles. Purified bovine synaptic vesicles (50 µg of protein) were suspended in the glutamate uptake assay medium in the presence of varying amounts of fraction 31 from the Mono Q column (0, 0.1, 0.2, 0.3, 0.4, 0.5, 0.65, 0.76, 0.86, 0.97, 1.1, 1.3, and 1.6 µg protein). Using a molecular weight of 138,000 for IPF α, these amounts were converted to 26 nmol IPF α/liter.

Uptake was allowed to proceed for 10 min at 30° C. Values for % of control were calculated relative to the ATP-dependent uptake in samples containing equivalent amounts of fraction 31 from a Mono Q gradient run in the absence of loaded protein.

A similar dose-response curve for IPF β was also generated and indicated an IC$_{50}$ of 24 nM (data not shown). At approximately 100 nM, both IPF α and β inhibited ATP-dependent glutamate uptake by 90%. However, neither IPF α nor IPF β had any effect on the ATP-independent component of glutamate uptake even at concentrations up to 100 nM (data not shown).

In order to investigate the specificity of the inhibitory effect produced by IPF, its effect on uptake in two other well characterized systems was examined: the Na$^+$-dependent glutamate uptake system in the synaptosomal plasma membrane and the ATP-dependent, reserpine-sensitive catecholamine uptake system in chromaffin vesicles from the adrenal medulla.

Figure 5:
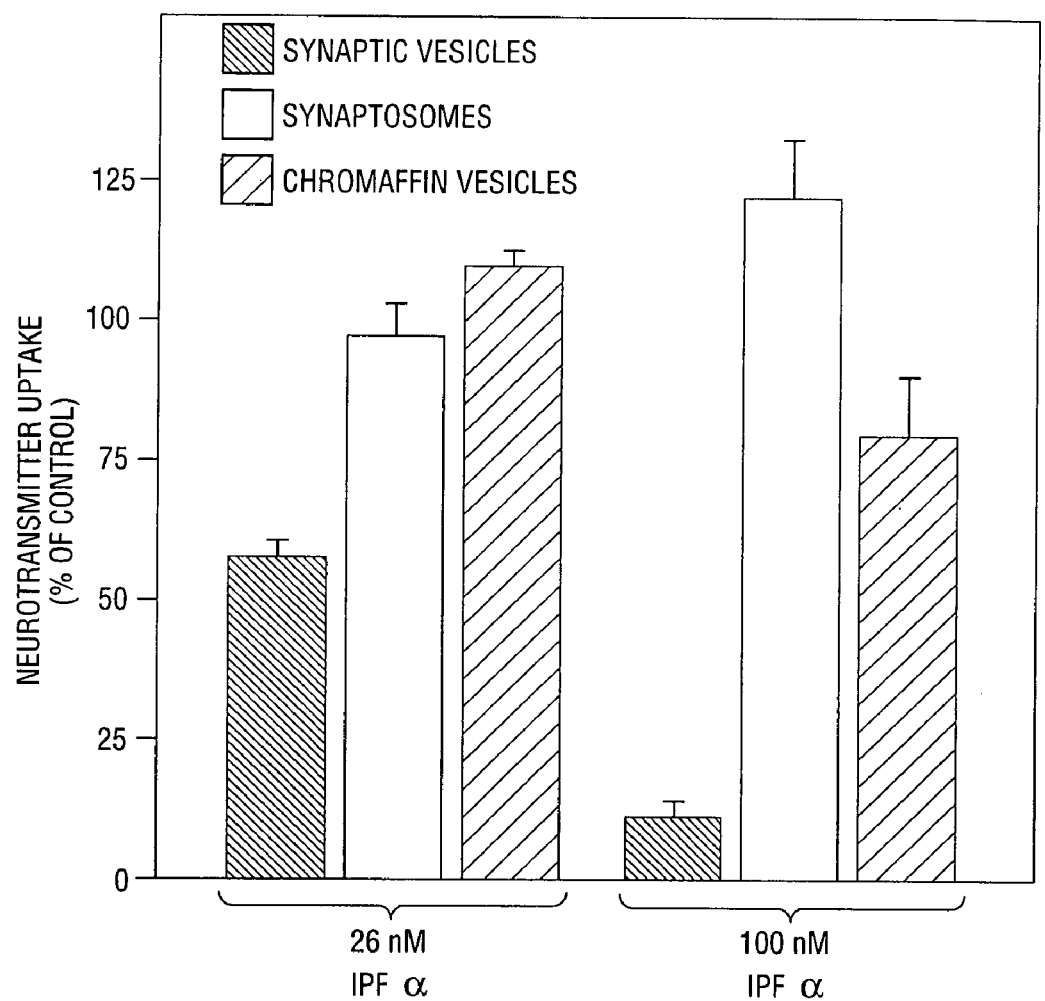
FIG. 5 graphically depicts the specificity of the inhibitory effect produced by IPF α.

FIG. 5 depicts the results of this examination. Bovine synaptic vesicles (50 μg of protein) were suspended in glutamate uptake assay medium. Bovine synaptosomes (35 μg protein) were suspended in 0.12 ml of Krebs-Ringer solution containing 1 mM spermine and 1 μM [$^3$H]glutamate (1.67 Ci/mmol) in the presence of Na$^+$ (150 mM) or choline (150 mM). Bovine chromaffin vesicles (45 μg protein) were suspended in 0.12 ml of a solution containing 0.3 M sucrose, 1 mM spermine, 10 mM MgSO$_4$, 5 mM ATP, 10 mM HEPES, pH 7.0 and 50 μM [$^3$H]norepinephrine (0.017 Ci/mmol) with or without 1 μM reserpine. Each membrane mixture also contained either 0, 26, or 100 nM IPF α. Glutamate uptake was allowed to proceed for 10 min at 30° C. and 30 min at 37° C. for norepinephrine uptake. Reaction was terminated by filtration as described in Methods. Values for % of control were calculated relative to the specific uptake activity obtained in the absence of IPF α. Uptake into synaptic vesicles is represented by ATP-dependent uptake, that into synaptosomes by Na$^+$-dependent uptake, and that into chromaffin vesicles by reserpine-sensitive uptake.

Results in FIG. 5 indicate that IPF α exhibited no inhibitory effect on Na$^+$-dependent glutamate uptake into bovine synaptosomes. Moreover, IPF α had only a minimal effect (~18% inhibition) on norepinephrine uptake into bovine chromaffin vesicle ghosts at 100 nM, a concentration that inhibited vesicular glutamate uptake by 90%.

The precise mechanism by which IPF leads to inhibition of vesicular glutamate uptake remains to be determined. Since transport of glutamate into synaptic vesicles is a coupled process, the possibilities for inhibiting such a system are multiplied by the number of potential coupling sites. Indirect modes of inhibition would include inhibiting the activity of the V-type H$^+$-ATPase, increasing the passive permeability of the vesicle membrane to protons, or causing a generalized increase in membrane permeability (a detergent-like effect). The results in FIG. 5 indicate that these possibilities are unlikely. If IPF were inhibiting the action of the V-type H$^+$-ATPase (either ATP hydrolysis or proton pumping), it would be expected that norepinephrine transport into chromaffin vesicles would also be inhibited. Similarly, any inhibitor which has a generalized protonophore activity would also lead to decreased uptake into chromaffin vesicles. FIG. 5 shows that norepinephrine transport is hardly affected by IPF concentrations up to 100 nM. Finally, the generalized increase in membrane permeability characteristically caused by detergents and other amphiphilic molecules should have an effect on glutamate storage in synaptosomes as well as on norepinephrine uptake. This was not observed.

Even though it has not been possible thus far to isolate purified GABAergic vesicles, preliminary experiments with mixed vesicle preparations (containing both glutamate and GABA uptake activities) have shown IPF to be just as potent an inhibitor of vesicular GABA uptake (data not shown).

Example 2

Characterization of IPF

Some of the physicochemical properties of IPF are summarized in Table II.

TABLE II

| Property | IPF α | IPF β | IPF γ |
|---|---|---|---|
| Relative Molecular Wt | 138,000 | 135,000 | 132,000 |
| Molecular Wt | 103,500 | — | — |
| Stokes Radius (angstroms) | 60 | 60 | 60 |
| Sedimentation Coefficient | 4.3 | 4.3 | 4.3 |
| Partial Specific volume (ml/gm) | 0.717 | — | — |
| Frictional ratio (f/f$_0$) | 1.67 | — | — |
| Axial ratio | 12 | — | — |
| IC$_{50}$ (nM) | 26 | 24 | — |

IPF α, β and γ share highly similar physicochemical properties. The relative apparent molecular weights determined by SDS-PAGE were 138, 135, and 132×10$^3$ for IPF α, β and γ, respectively. Their Stokes radii and sedimentation coefficients were indistinguishable from each other, being 60 Å and 4.3S, respectively. The partial specific volume of IPF α was calculated to be 0.717 ml/g from amino acid composition. Using these values, an approximate molecular weight of IPF α in the native form was calculated to be 103,000, according to the equation M=6 πηNas/(1-ῡρ), where N=Avogadro's number, η=viscosity of water at 20° C., a=Stokes radius, s=sedimentation coefficient at 20° C., ῡ=partial specific volume, and ρ=density of water at 20° C. [Siegel and Monty (1966) Biochim. Biophys. Acta 112, 346–362]. This molecular weight is significantly smaller than that determined by SDS-PAGE. The excessively high Stokes radius and low sedimentation coefficient values for a globular protein indicate that IPF has an elongated shape. This is in agreement with the rather high axial ratio of 12 estimated from the calculated frictional coefficient ratio of 1.67.

Calculations utilizing the Stokes radius, sedimentation coefficient, and partial specific volume for IPF α indicate a native molecular mass of 103 kDa. This is at odds with the apparent molecular weight of 138,000 determined by SDS-PAGE. Additionally, the unexpectedly low sedimentation coefficient of 4.3 S is not consistent with the large Stokes radius (60 Å). These data collectively indicate that IPF α is a protein with a markedly elongated structure. This hypothesis is further supported by the large frictional coefficient and axial ratio (see Table II) determined for IPF α and by the relationship to α fodrin, itself a linear protein. How this rather eccentric structural characteristic might contribute to the ability to inhibit glutamate uptake is not known. The differences in charge between IPF α and IPF β, which render them separable by ion-exchange HPLC (see FIG. 3), apparently have little effect on inhibitory activity, as the two proteins share similar $IC_{50}$ values.

FIG. 6A (SEQ ID NO:5) gives the results of partial sequencing of IPF α. N-terminal sequencing revealed that amino acids 1–20 of IPF α,β and γ are identical with amino acids 26–45 of human α fodrin. Four further peptides (amino acids 393–415, 621–636, 965–974, and 1086–1095) generated by partial digestion of IPF α confirmed the relationship to α fodrin. Amino acid sequences determined for IPF α are shown in boldface in FIG. 6A within the initial 1200 amino acid residues of human α fodrin as determined by Moon and McMahon [(1990) *J. Biol. Chem.* 265, 4427–4433]. The 20-mer beginning with $Tyr^{26}$ represents the N-terminus of IPF α. The four internal sequences were determined by sequencing peptides produced by proteolytic digestion of IPF α. The highlighted bond between $Tyr^{1176}$ and $Gly^{1177}$ represents the cleavage site for calpain [Harris et al. (1988) *J. Biol. Chem.* 263, 15754–15761]. FIG. 6B (SEQ ID NO:6) shows the predicted sequence of IPF based upon sequencing of the N-terminus and the cleavage site for calpain as the C-terminus. Based upon this sequence, IPF α is estimated to have a true molecular weight of about 133 kD.

Despite this relationship, fodrin purified from wholebrain, according to the method described by Cheney et al. [(1986) *Meth. Enzymol.* 134, 42–54], had no effect on glutamate uptake at concentrations up to 1 μM (data not shown).

Example 3

Treatment of IPF with Trypsin

Figure 7:
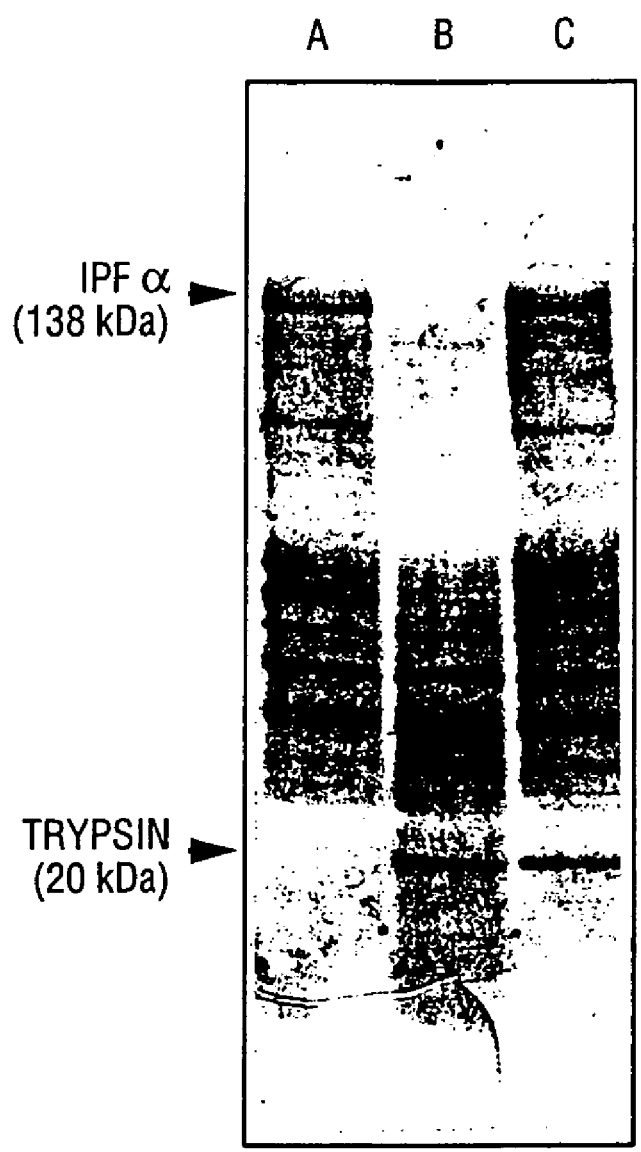
FIG. 7 shows the effect of trypsin exposure on IPF. Lane A shows the SDS-PAGE profile of the partially purified IPF composition without trypsin treatment. Lane B shows the SDS-PAGE profile of the partially purified IPF composition with trypsin treatment. It is clear that the 138 kD IPF band is not present, demonstrating the digestion of IPF by trypsin. Lane C shows the SDS-PAGE profile of the partially purified IPF composition in the presence of trypsin and pancreatic trypsin inhibitor.

IPF partially isolated as described in Example 1 was further treated by incubation at 30° C. for five minutes in the presence of trypsin (0.1 μg). FIG. 7 shows the effect of trypsin exposure on IPF. Lane A shows the SDS-PAGE profile of the partially purified IPF composition without trypsin treatment. Lane B shows the SDS-PAGE profile of the partially purified IPF composition with trypsin treatment. It is clear that the 138 kD IPF band is not present, demonstrating the digestion of IPF by trypsin. Lane C shows the SDS-PAGE profile of the partially purified IPF composition obtained in the presence of trypsin and pancreatic trypsin inhibitor. Thus, it is clear that treatment of IPF with trypsin induces digestion of the IPF proteins.

Figure 8:
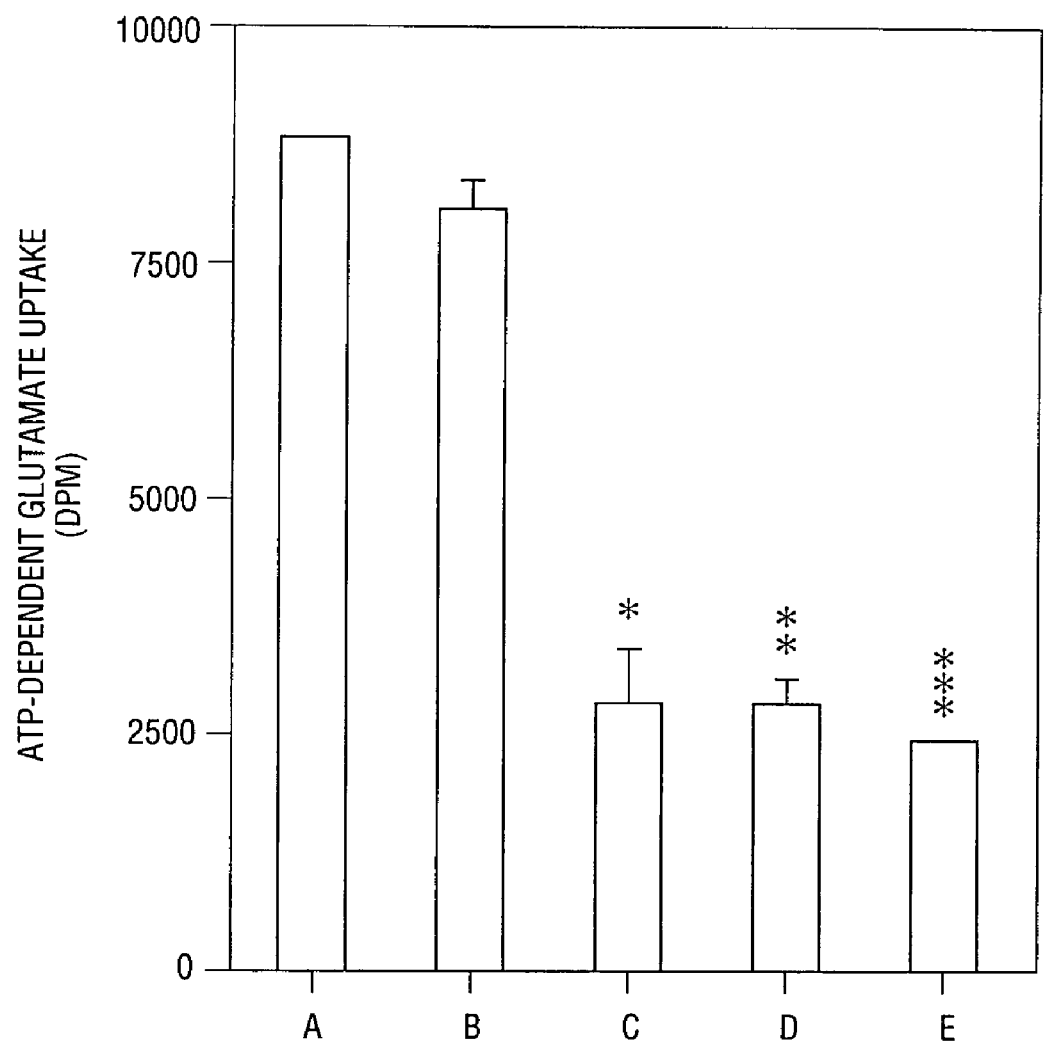
FIG. 8 depicts the results of the fractions obtained from FIG. 7. Lane A depicts control glutamate uptake without additives. Lane B depicts glutamate uptake by synaptic vesicles in the presence of trypsin and pancreatic trypsin inhibitor. Lane C depicts glutamate uptake by synaptic vesicles in the presence of partially purified IPF. Lane D depicts glutamate uptake by synaptic vesicles in the presence of partially purified IPF and trypsin. Lane E depicts glutamate uptake by synaptic vesicles in the presence of partially purified IPF, trypsin and pancreatic trypsin inhibitor.

The impact of trypsin digestion on glutamate uptake inhibition in synaptic vesicles was then determined. FIG. 8 depicts these results. Lane A depicts control glutamate uptake without additives. Lane B depicts glutamate uptake by synaptic vesicles in the presence of trypsin and pancreatic trypsin inhibitor. Lane C depicts glutamate uptake by synaptic vesicles in the presence of partially purified IPF. Lane D depicts glutamate uptake by synaptic vesicles in the presence of partially purified IPF and trypsin. Lane E depicts glutamate uptake by synaptic vesicles in the presence of partially purified IPF, trypsin and pancreatic trypsin inhibitor. While Lanes A and B show no significant glutamate uptake inhibition, both the unfragmented IPF in Lanes C and E and the trypsin fragmented IPF of Lane D showed glutamate uptake inhibition. Thus, it is clear that one or more products resulting from trypsin digestion of IPF inhibit glutamate uptake by synaptic vesicles.

Example 4

Animal Model for In Vivo Drug Screening

As described above, the present invention contemplates the use of synaptic vesicle glutamate uptake inhibitors for the treatment of neurosynaptic disorders. Screening of glutamate uptake inhibitors for in vivo-efficacy can be performed in the context of animal models. One animal model is the Epileptic (EL) mouse.

The seizures in EL mice are inherited as a multifactorial trait and are considered model for human complex partial seizures with secondary generalization [Rise et al. (1991) *Science* 253 669–73]. The seizures in EL mice occur spontaneously or can be induced by rhythmic vestibular stimulation [Kurokawa et al. (1966) *Prog. Brain Res.* 21A 112–30]. The seizures in EL mice generally begin at 80 to 100 days of age and are thought to originate in or near the parietal lobe and then spread quickly to the hippocampus and to other brain regions [Seyfried (1992) *Neurosciences* 18 (Suppl. 2) 9–20].

In this example, it is shown that synaptic vesicle glutamate uptake is increased in a brain region-specific manner in epileptic (EL) mice as compared to age matched non-epileptic control mice. This increase was observed at an age when EL mice express handling-induced seizures, but it was not seen in young EL mice prior to seizure onset. The findings could reflect an increase in glutamatergic synaptic vesicle number, with or without a change in the number of nerve terminals, or alternatively an increase in the number of nerve terminals without an increase in vesicles per terminal. A combination of these mechanisms might also be involved. It is also possible that this increase is due to alterations in the synaptic vesicle such as regulation of transport by chloride or an internal volume change in the synaptic vesicle.

Synaptic vesicles isolated from various brain regions in EL mice prior to (46 days old) and after (approx. 400 days old) the onset of handling or spontaneous seizures are studied. The EL mice were compared to age-matched non-epileptic control mice (DDY and APB).

Synaptic vesicles were prepared from four brain regions: cerebrum (minus hippocampus), hippocampus, cerebellum and brain stem. The cerebrum therefore contains the entire cerebral cortex, except for the hippocampus. Each preparation represents the synaptic vesicles from one mouse with the exception of the hippocampus, where each preparation represents 1–2 mice. Each tissue preparation represents different mice.

In brief, brain tissue was homogenized in solution A (0.32 M sucrose, 0.5 mM calcium acetate, 1 mM magnesium acetate and 1 mM $NaHCO_3$). The homogenate was centrifuged at 10,000 rpm in a Sorvall SM-24 rotor for 20 minutes. The pellets were lysed for 45 minutes in 6 mM Tris-maleate (pH 8.1) and centrifuged at 19,000 rpm in a Sorvall SM-24 rotor for 15 minutes. The supernatant was centrifuged at 43,000 rpm in a Beckman Ti45 rotor for 70 minutes, and the crude synaptic vesicles were resuspended in solution B (0.32 M sucrose, 1 mM dithiothreitol and 1 mM $NaHCO_3$). Synaptic vesicles were stored in liquid nitrogen until use, typically within one week. Synaptic vesicles prepared in this manner exhibited properties essentially indistinguishable from those observed with highly purified preparations.

Synaptic vesicle uptake activity was determined by the method described above. In the old mice, glutamate uptake activity was significantly increased in the EL mice cerebellum (minus hippocampus) compared to the control DDY mice. No difference was observed between EL and control DDY mice in the other brain areas. In younger mice, no significant difference in ATP-dependent glutamate uptake activity was observed either in the cerebrum (minus hippocampus) or in the brain stem. These results are set forth in Table III.

TABLE III

Vesicular Uptake in EL and Control Non-Epileptic Mice

| Strain | Days Old | Cerebrum (pmol/mg protein) | Hippo-camp (pmol/mg protein) | Cerebellum (pmol/mg protein) | Brain Stem (pmol/mg protein) |
|---|---|---|---|---|---|
| EL | 411 ± 10 | 1230 ± 59 | 766 ± 107 | 358 ± 55 | 466 ± 66 |
| DDY | 395 ± 8 | 813 ± 69 | 689 ± 88 | 316 ± 11 | 374 ± 43 |
| ABP | 424 ± 6 | 796 ± 64 | 632 ± 123 | N.D. | N.D. |
| EL | 46 ± 0 | 941 ± 61 | N.D. | N.D. | 872 ± 119 |
| DDY | 46 ± 0 | 906 ± 84 | N.D. | N.D. | 1078 ± 181 |

The data suggest that ATP-dependent glutamate uptake increases in response to seizures. No difference were found between epileptic and non-epileptic mice prior to the onset of seizures (46 days old). The ATP-dependent glutamate uptake was increased in the epileptic mice in a brain-region specific manner at an age when the EL mice had a long seizure history. The data therefore suggest that the increased synaptic vesicle glutamate uptake in EL mice is not the initial cause of seizure development, but either an effect of the seizures or the cause of continued seizures.

Previous studies of glutamate levels in EL mice were concerned with changes in the total levels in brain tissue, including pools for both metabolism and synaptic release. It was difficult to draw coherent conclusions from some of these studies, as the results were not always consistent. Since the neurotransmitter pool represents a small portion of the total tissue glutamate content, these changes may not directly reflect changes in the levels of glutamate to be released as a neurotransmitter. Recent findings suggest that enhanced aspartate release may be genetically associated with seizure susceptibility in EL mice.

While no differences were observed in other brain regions between epileptic and nonepileptic mice, it was observed that ATP-dependent glutamate uptake activity in the brain stem was higher in the 46 day old mice compared to the 400 day old mice. It is likely that this relates to maturation effects. It is unlikely that this relates to seizure development, as the control strain demonstrated uptake activity indistinguishable from that observed in the epileptic strain, regardless of age.

Example 5

Polyclonal Antibodies to IPF

In this example, antibodies were raised that were demonstrated to be reactive with both intact fodrin and a fodrin fragment (i.e. IPF alpha). Moreover, following absorption of the antibody mixture on column of immobilized intact fodrin, antibodies reactive with intact fodrin were removed, leaving antibodies only reactive with the fodrin fragment.

Polyclonal antibodies to a decapeptide having a sequence corresponding to the N-terminal sequence of IPF α (anti-IPF α) were made in rabbits. The total protein from 50 ug Cytosol were then separated on SDS-PAGE. One strip of the gel was stained with Coomassie Blue. The proteins in the remaining portion of the gel were transferred to nitrocellulose, the nitrocellulose was temporarily stained to visualize the lanes, destained, and blocked. The blot was cut into strips and each strip incubated with the appropriate primary antibody. After washing in buffer, antibody binding was visualized using a goat anti-rabbit IgG conjugated to alkaline phosphatase from Bio-Rad.

Figure 9A:
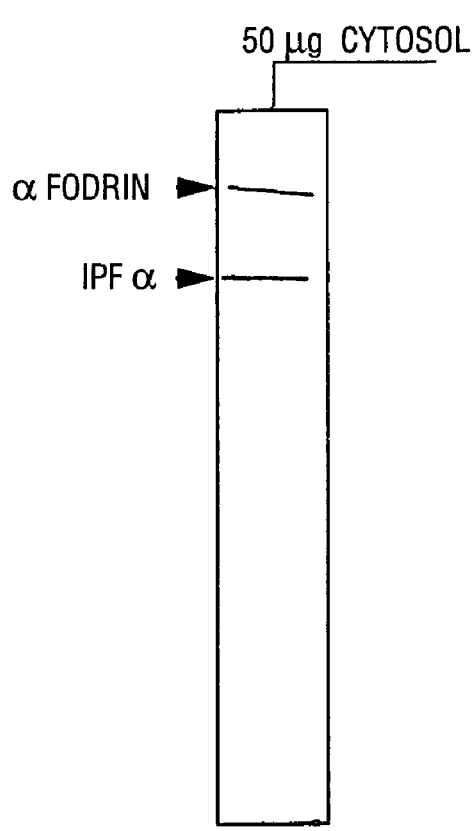
FIG. 9 depicts the results of Western Blot assays of antibodies raised to a fodrin decapeptide. Panel A demonstrates the binding of antibodies to both fodrin and IPF, while Panel B demonstrates binding of antibodies to IPF without binding to fodrin.
Figure 9B:
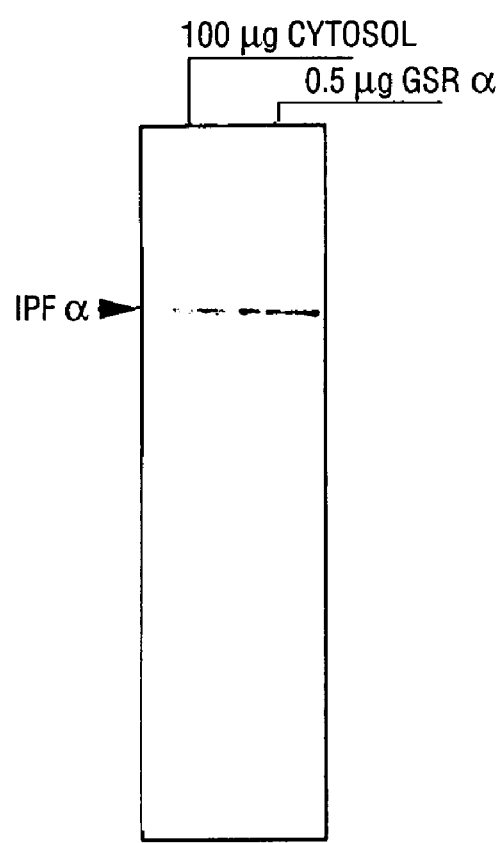

The results of the immunoblotting are shown in FIG. 9. Panel A is a 7.5% polyacrylamide gel and containing 50 micrograms of cytosol. In this gel, the sample was probed with a 1:2000 dilution of unabsorbed rabbit anti-decapeptide. The gel shows that the unabsorbed antibody reacts with both intact fodrin and IPF α.

The antibody used in Panel A was thereafter absorbed on a column containing purified fodrin coupled to sepharose 4B. Total protein from a 100 ug Cytosol preparation was run (along with IPF alpha) on a gel (6.0% polyacrylamide gel) and transferred to nitrocellulose. The immunoblot was probed with a 1:1000 dilution of antiserum. The results are shown in Panel B. The immunoblot shows binding of antibody to IPF α but no antibody binding to intact fodrin. This suggests that the conformation of intact fodrin is such that at least a portion of the region represented by the decapeptide is sterically hidden.

Based upon the description and experimental materials presented above, it is clear that the present invention provides compositions and method for the treatment of neurosynaptic disorders in a subject.

We claim:

1. A method for assessing overcoming synaptic vesicle glutamate uptake inhibition activity, comprising
   a) providing:
      i) synaptic vesicles,
      ii) a composition comprising a purified fordin fragment having glutamate uptake inhibition activity, said fragment having an N-terminus and a C-terminus, wherein said N-terminus is Tyr26 of fodrin, and
      iii) a candidate compound; and
   b) combining said candidate compound with said synaptic vesicles and said fragment such that the effect of said candidate compound on glutamate uptake by said vesicle can be assessed.

2. The method of claim 1, wherein said purified fragment comprises IPF α.

3. The method of claim 1, wherein said purified fragment comprises IPF β.

4. The method of claim 1, wherein said purified fragment comprises IPF γ.

5. A method for assessing overcoming synaptic vesicle glutamate uptake inhibition activity, comprising
   a) providing:
      i) synaptic vesicles,
      ii) a composition comprising a purified fragment of IPF having synaptic vesicle glutamate uptake inhibition activity, said fragment having an N-terminus and a C-terminus, wherein said N-terminus is Tyr26 of fodrin, and
      iii) a candidate compound; and
   b) combining said candidate compound with said synaptic vesicles and said fragment such that the effect of said candidate compound on glutamate uptake by said vesicle can be assessed.

6. The method of claim 5, wherein said fragment comprises a fragment of IPF α.

7. The method of claim 5, wherein said fragment comprises a fragment of IPF β.

8. The method of claim 5, wherein said fragment comprises a fragment of IPF γ.

9. The method of claim 1, wherein said purified fragment comprises a fragment of IPFα.

10. The method of claim 5, wherein said purified fragment comprises a fragment of IPFα.

11. A method for assessing overcoming synaptic vesicle glutamate uptake inhibition activity, comprising:
 a) providing:
  i) synaptic vesicles,
  ii) a composition comprising a purified fragment of fodrin having glutamate uptake inhibition activity, said fragment having an N-terminus and a C-terminus, wherein said purified fragment comprises a peptide having the amino acid sequence EAALTSEEVG within 150 amino acids of the C-terminus of the peptide, and
  iii) a candidate compound; and
 b) combining said candidate compound with said synaptic vesicles and said fragment such that the effect of said candidate compound on glutamate uptake by said synaptic vesicles can be assessed.

12. A method for assessing overcoming synaptic vesicle glutamate uptake inhibition activity, comprising:
 a) providing:
  i) synaptic vesicles,
  ii) a composition comprising a purified peptide having glutamate uptake inhibition activity with an N-terminus sequence comprising the amino acid sequence YHRFK, and
  iii) a candidate compound; and
 b) combining said candidate compound with said synaptic vesicles and said fragment such that the effect of said candidate compound on glutamate uptake by said synaptic vesicles can be assessed.

13. The method of claim 12, wherein said purified peptide has an N-terminus comprising the amino acid sequence YHRFKELSTL (SEQ ID NO:3).

14. The method of claim 13, wherein said purified peptide has an N-terminus comprising the amino acid sequence YHRFKELSTLRRQKLEDSYR (SEQ ID NO:4).

* * * * *